(12) United States Patent
Seul et al.

(10) Patent No.: US 9,436,088 B2
(45) Date of Patent: *Sep. 6, 2016

(54) UN-SUPPORTED POLYMERIC FILM WITH EMBEDDED MICROBEADS

(75) Inventors: Michael Seul, Fanwood, NJ (US); Sukanta Banerjee, North Brunswick, NJ (US); Kairali Podual, North Brunswick, NJ (US); Ye Hong, Piscataway, NJ (US)

(73) Assignee: BioArray Solutions, Ltd., Warren, NJ (US)

(*) Notice: Subject to any disclaimer, the term of this patent is extended or adjusted under 35 U.S.C. 154(b) by 843 days.

This patent is subject to a terminal disclaimer.

(21) Appl. No.: 11/761,789

(22) Filed: Jun. 12, 2007

(65) Prior Publication Data

US 2007/0248993 A1    Oct. 25, 2007

Related U.S. Application Data

(63) Continuation of application No. 10/034,727, filed on Dec. 26, 2001, now Pat. No. 7,262,063.

(60) Provisional application No. 60/300,025, filed on Jun. 21, 2001.

(51) Int. Cl.
  *G01N 33/553* (2006.01)
  *G03F 7/16* (2006.01)
  *G03F 7/004* (2006.01)

(52) U.S. Cl.
  CPC .............. *G03F 7/164* (2013.01); *G03F 7/0047* (2013.01); *Y10T 428/249952* (2015.04); *Y10T 428/25* (2015.01)

(58) Field of Classification Search
  CPC ... G03F 7/164; G03F 7/0047; Y10T 428/25; Y10T 428/249952
  USPC ........................................................ 436/526
  See application file for complete search history.

(56) References Cited

U.S. PATENT DOCUMENTS 3,329,638 A    7/1967  Blyth
3,574,614 A    4/1971  Carreira
(Continued)

FOREIGN PATENT DOCUMENTS

CA    1248873    1/1989
DE    4035714    5/1992
(Continued)

OTHER PUBLICATIONS

Armstrong et al., "Suspension arrays for high throughput, multiplexed single nucleotide polymorphism genotyping" Cytometry. vol. 40:102-108 (2000).
(Continued)

*Primary Examiner* — Mark Shibuya
*Assistant Examiner* — Pensee Do
(74) *Attorney, Agent, or Firm* — Mintz, Levin, Cohn, Ferris, Glovsky and Popeo P.C.

(57) ABSTRACT

The present invention relates to polymer-bead composites having a single layer planar, crystalline assembly of encoded beads embedded in a hydrophilic polymeric matrix. The composite may be unattached to a solid support. The encoded beads have different biomolecules attached to their surfaces, and the encoding permits distinguishing beads having different biomolecules attached thereto. The present invention also relates to a systematic process for the creation of functionally organized, spatially patterned assemblies of polymer-microparticle composites, including the AC electric field-mediated assembly of patterned, self-supporting organic (polymeric) films and organic-polymer-microparticle composites of tailored composition and morphology. The present invention also relates to the application of such functional assemblies in materials science and biology. Additional areas of application include sensors, catalysts, membranes, and micro-reactors, and miniaturized format for generation of multifunctional thin films.

8 Claims, 20 Drawing Sheets

(56) References Cited

U.S. PATENT DOCUMENTS

| | | |
|---|---|---|
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | MacEvicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |

(56) References Cited

U.S. PATENT DOCUMENTS

| | | |
|---|---|---|
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Wiley |
| 5,643,765 A | 7/1997 | Wiley |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | Van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforoy et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A * | 11/1999 | Rasmussen et al. .......... 428/120 |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |

(56) References Cited

U.S. PATENT DOCUMENTS

| | | |
|---|---|---|
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | McBride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 * | 10/2001 | Gombinski .................. 436/526 |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B2 | 2/2003 | Lee et al. |
| 6,514,771 B1 * | 2/2003 | Seul .............. 436/518 |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauvar et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 * | 6/2005 | Sammak et al. .............. 436/172 |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,118,900 B2 * | 10/2006 | Seul et al. .................... 435/182 |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,262,063 B2 * | 8/2007 | Banerjee et al. .............. 436/524 |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 * | 4/2008 | Seul et al. .................... 436/518 |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 * | 11/2009 | Seul .................... B01J 19/0046 435/283.1 |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |

(56) References Cited

U.S. PATENT DOCUMENTS

| | | |
|---|---|---|
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1* | 11/2001 | McGall et al. ............ 536/26.1 |
| 2001/0046602 A1 | 11/2001 | Chandler et al. |
| 2001/0049095 A1 | 12/2001 | Webster |
| 2002/0006634 A1* | 1/2002 | Han et al. ............... 435/25 |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |
| 2003/0087228 A1 | 5/2003 | Bamdad et al. |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| WO | WO8911101 | 5/1989 |
| WO | WO 9109141 | 6/1991 |
| WO | WO 9119023 | 12/1991 |
| WO | WO 9210092 | 6/1992 |
| WO | WO 9302360 | 2/1993 |
| WO | WO 9306121 | 4/1993 |
| WO | WO 9324517 | 12/1993 |
| WO | WO 9325563 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |

(56) References Cited

FOREIGN PATENT DOCUMENTS

| | | |
|---|---|---|
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO02057496 | 7/2002 |
| WO | WO02058379 | 7/2002 |
| WO | WO02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |
| WO | WO2010026038 | 3/2010 |
| WO | WO2010098765 | 9/2010 |
| WO | WO 2010143678 | 12/2010 |

OTHER PUBLICATIONS

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).
B.-Y. Ha et al., "Counterion-Mediated Attraction between Two Like-Charged Rods," Physical Review Letters, Aug. 18, 1997, vol. 79, No. 7, pp. 1289-1292.
A. Hatch, et al., "Diffusion Immunoassay in Polyacrylamide Hydrogels". Micro Total Analysis Systems, pp. 571-572 (2001).
Aho et al., "Efficient String Matching: An Aid to Bibliographic Search". Communications of the ACM, vol. 18, No. 6, pp. 333-340 (Jun. 1975).
Albergo et al., "Solvent effects on the thermodynamics of double-helix formation in (dG-sC) 3". Biochemistry, vol. 20, No. 6: 1413-1418 (1981).
Albrecht et al, "Probing the role of multicellular organization in three-dimensional microenvironments". Nature Methods, vol. 3, No. 5, pp. 369-375 (May 2006).
Albrecht et al., "Photo and electropatterning of hydrogel-encapsulated living cell arrays", Lab on a Chip, vol. 5, Issue 1, pp. 111-118 (2004).
Alford, R. L., "DNA Analysis in forensics, disease and animal/plant identification". Current Opinions in Biotechnology, vol. 5(1), pp. 29-33 (1994).
Al-Soud, W. A., "Purification and Characterization of PCR-Inhibitory Components in Blood Cells". Journal of Clinical Microbiology, vol. 39, No. 2, pp. 485-493 (Feb. 2001).
Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94-98.
Zhang, Y., et al., "Reproducible and inexpensive probe preparation for oligonucleotide arrays". Nucleic Acids Research, vol. 29, No. 13, pp. E66-6 (Jul. 1, 2001).
Arenko, et al., "Protein microchips: Use for immunoassay and enzymatic reactions". Analytical Biochemistry, vol. 278, pp. 123-131 (2000).
Assie et al., Correlation between low/high affinity ratios for 5-HT Receptors and Intrinsic Activity, European Journal of Pharmacology, vol. 386, pp. 97-103 (1999).
Bakewell et al., "Characterization of the dielectrophoretic movement of DNA in micro-fabricated structures", Institute of Physics Conference Series (1999) Electrostatics (1999).
Balass et al. "Recovery of high-affinity phage from a Nitrostretavidin matrix in phage-display technology". Analytical Biochemistry. vol. 243: 264-269 (1996).
Baldwin, et al., "Phosphorylation of gastrin-17 by epidermal growth factor-stimulated tyrosine kinase". Nature, vol. 44, pp. 2403-2404 (1998).
Bandeira-Melo, C., et al., "EliCell: A gel-phase dual antibody capture and detection assay to measure cytokine release from eosinophils". Journal of Immunological Methods, vol. 244, pp. 105-115 (2000).
Bao, Y. P., et al., "Detection of Protein Analytes via Nanoparticle-Based Bio Bar Code Technology". Anal. Chem., vol. 78, pp. 2055-2059 (2006).
Barany, Francis, "Genetic Disease Detection and DNA Amplification using Cloned Thermostable Ligase". Proceedings of the National Academy of Sciences of the United States of America, vol. 88, pp. 189-193 (Jan. 1991).
Barnard et al. "A fibre-optic chemical sensor with descrete sensing sites". Nature, vol. 353:338-340 (1991).
Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).
Battersby et al., "Toward Larger Chemical Libraries: Encoding with Fluorescent Colloids in Combinatorial Chemistry". J. Amer Chem Soc, vol. 122, pp. 2138-2139 (2000).
Baumgarth N. et al., A practical approach to multicolor flow cytometry for immunophenotyping, J. Immunological Methods, 2000, pp. 77-97, vol. 243.
Bavykin, S.G., et al., "Portable system for microbial sample preparation and oligonucleotide microarray analysis". Appl. Environmental Microbiol. 67(2), 922-928 (2001).
Beatty et al. "Probability of Finding HLA-mismatched Related or Unrelated Marrow or Cord Blood Donors", Human Immunology, 2001, vol. 61, pp. 834-840.
Beebe et al., "Functional Hydrogel structures for autonomous flow control inside microfluidic channels". Nature, vol. 404, No. 6778, pp. 588-590 (Apr. 6, 2000).
Beiboer, S. W., et al., "Rapid genotyping of blood group antigens by multiplex polymerase chain reaction and DNA microarray hybridization" 45 Transfusion 667-679 (2005).
Bennett, P. R., et al., "Prenatal Determination of Fetal RhD Type by DNA Amplification". The New England Journal of Medicine, vol. 329, No. 9, pp. 607-610 (Aug. 26, 1993).
Bernard, Philip S., "Homogenous Multiplex Genotyping of Hemochromatosis Mutations with Fluorescent Hybridization Probes". American Journal of Pthology, vol. 153, No. 4, pp. 1055-1061 (1998).
Bessetti, J., "An introduction to PCT Inhibitors". Profiles in DNA-PCR Inhibition, pp. 9-10 (Mar. 2007).
Bickel, P. J., "Discussion of the Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).

(56) References Cited

OTHER PUBLICATIONS

Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Camplan et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. (1995). The Bipohysics of DNA Hybridization with Immobilized Oligonucleotide Probes. Biophysical Journal 69:2243-2255.
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, page est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/percond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a small) dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).

(56) References Cited

OTHER PUBLICATIONS

Decher, G., "Fuzzy Nanoassemblies: Toward Layered Polymeric Multicomposites". Science, vol. 277, pp. 1232-1237 (Aug. 29, 1997).
Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibllity Determination. I. Description of the Algorithm. Human Immunology, vol. 63, pp. 339-352 (2002).
Dziennik, S. R., et al., "Nondiffusive mechanisms enhance protein uptake rates in Ion exchange particles". PNAS, vol. 100, No. 2, pp. 420-425 (2003).
Easteal, S. "DNA Fingerprinting by PCR Amplification of HLA Genes". DNA and Criminal Justice. 1991; Human Genetics Group, John Curtin School of Medical Research, pp. 121-127.
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al. "Rapid Development of Nucleic Add Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).

Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Dg Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790.
Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2002;7(10):569-79.

(56) References Cited

OTHER PUBLICATIONS

Gustafsdottir, S. M., "In vitro analysis of DNA-protein interactions by proximity ligation". PNAS, vol. 104, No. 9, pp. 3067-3072 (Feb. 2007).
Haab et al. Single Molecule Fluorescence Burst Detection of DNA Fragments Separated by Capillary Electrophoresis. Analytical Chemistry, vol. 67 (No. 18) : 3253-3256 (1995).
Hacis et al., "Resequencing and mutational analysis using oligonucleotide microarrays", Nature America; 21 : 42-47 (1999).
Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).
Hashimi et al., "A Flexible Array format for large-scale, rapid blood group DNA typing". Transfusion, Published Online Apr. 6, 2004, vol. 45, Issue 5, pp. 680-688 (May 2005).
Hashmi, G., et al, "Determination of 24 minor red blood cell antigens for more than 2000 blood donors by high-throughput DNA analysis". Transfusion, vol. 47, No. 4, pp. 736-747 (Apr. 2007).
Zaer, Farld, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).
Heinrich, et al., "Interleukin-6-type Cytokine Signaling through the gp 130/Jak/STAT pathway". Biochem J, vol. 334, pp. 297-314 (1998).
Helgesen, et al., "Aggregation of magnetic microspheres: experiements and simulations". Physical Review Letters, vol. 61, No. 15, pp. 1736-1739 (1998).
Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).
Yershov et al., "DNA analysis and diagnostics on oligonulceotide microchips". Proceedings of the National Academy of Sciences of the United States of America, vol. 93, No. 10, pp. 4913-4918 (May 14, 1996).
Hiller, J., et al., "Reversibly erasable nanoporous anti-reflection coatings from polyelectrolyte multilayers". Nature Materials, vol. 1, pp. 59-63 (Sep. 2002).
Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).
Hizume, et al., "Tandem repeat DNA localizing on the proximal DAPI bands of chromosomes in Larix, pinaceae". Genome, vol. 45, pp. 777-783 (2002).
Holtz, J., et al., "Intelligent Polymerized Crystalline Colloidal Array: Novel Sensor Materials", Analytical Chemistry, vol. 70, No. 4, pp. 780-791 (1998).
Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).
Huff et al., "Technical Milestone: Development of the Logical Observation Identifier Names and Codes (LOINC) Vocabulary". JAIMA, vol. 5, pp. 276-292 (1998).
Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).
Ide et al., "Synthesis and damage specificity of a novel probe for the detection of abasic sites in DNA". Biochemistry. vol. 32: 8276-8283 (1993).
Ito, Y., et al., "Patterned Immobilization of Thermoresponsive Polymer", Langmuir, vol. 13, pp. 2756-2759 (1997).
Iwayama, et al., "Optically Tunable Gelled Photonic Crystal Covering Almost the Entire Visible Light Wavelength Region", Langmuir (2002).
Jackman, R. J., et al., "Using Elastomeric Membranes as Dry Resists and for Dry Lift-Off", Langmuir, vol. 15, pp. 2973-2984 (1999).
Jeon, N. L., et al., "Patterned polymer growth on silicon surfaces using microcontact printing and surface-initiated polymerization", Applied Physics Letters, vol. 75, No. 26, pp. 4201-4203 (1999).
John C. Guatelli et al., "Isothermal, in vitro amplification of nucleic acids by a multienzyme reaction modeled after retroviral replication," Proc. Nat'l Academy of Science USA, vol. 87: pp. 1874-1878 (1990).
Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).
Jones et al., "Constraint, Optimization, and Hierarchy: Reviewing Stereoscopis Correspondence of Complex Features". Computer Vision and Image Understanding, vol. 65, No. 1, pp. 57-78 (1997).
Jones et al., "Dielectrophoretic liquid actuation and nanodroplet formation", Journal of Applied Physics, vol. 89, No. 2, pp. 1441-1448 (Jan. 15, 2001).
Kakabakos et al. "Immobilization of Immunoglobulins onto Surface-treated and Untreated Polystyrene Beads for Radioimmunoassays" Clin. Chem. 36 (1990), 492-496.
Kalinina, O., et al., "A core-shell Approach to Producing 3D Polymer Nanocomposites", Macromolecules, vol. 32, pp. 4122-4129 (1999).
Kamholz, et al., "Optical measurement of transverse molecular diffusion in a microchannel". Biophysical Journal, vol. 80, pp. 1967-1972 (2001).
Kamm, R. C., et al. "Nucleic Acid Concentrations in Normal Human Plasma". Clinical Chemistry, vol. 18, pp. 519-522 (1972).
Kandimalla et al., "Cyclicons" as Hybridization-Based Fluorescent Primer-Probes: Bioorganic & Medicinal Chemistry 8 (2000) 1911 to 1916.
Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).
Klintschar, et al., "Genetic variation at the STR loci D12S391 and CSF1PO in four populations from Austria, Italy, Egypt and Yemen". Forensic Sci. Int. vol. 97:37-45 (1998).
Kim, E., et al., "Polymer microstructures formed by moulding in capillaries", Nature, vol. 376, pp. 581-584 (1995).
Knipper, et al., Accession No. AF221125.1.1 on Electronic Database at NCBI (Feb. 16, 2000).
Koch et al., "PNA-Peptide Chimerae". Tetrahedron Letters, vol. 36, pp. 6933-6936 (1995).
Koh, et al., "Molding of Hydrogel Microstructures to Create Multiphenotype Cell Microarrays". Analytical Chemistry (2003).
Koh, et al., "Poly(ethylene glycol) Hydrogel Microstructures Encapsulating Living Cells". Langmuir, vol. 18, pp. 2459-2462 (2002).
Kolch. "Meaningful Relationships: The Regulation of the Ras/Raf/MEK/ERK pathway by protein interactions". Biochem J, vol. 351, pp. 289-305 (2000).
Kotov, N., et al., "Layer-by-Layer Self-Assembly of Polyelectrolyte-Semiconductor Nanoparticle Composite Films". J. Phy Chem, vol. 99, pp. 13065-13069 (1995).
Krausa et al. "A Comprehensive PCR-ssP typing system for identification of HLA-A locus alleles", Tissue Antigens, 47 (3) : 237-244 (1996).
Krsko, P., et al., "Electron-Beam Surface Patterned Poly(ethylene glycol) Microhydrogels". Langmuir, vol. 19, pp. 5618-5625 (2003).
Krutzik P.O. et al., "Fluorescent cell barcoding in flow cytometry allows high-throughput drug screening and signal profiling". Nature Methods, vol. 3, No. 5, pp. 361-368 (2006).
Kubo et al., "A Novel Sensitive and specific assay for abasic sites, the most commonly produced DNA lesion". Biochemistry, vol. 13:3703-3708 (1992).
Kumacheva, E., et al., "Three-dimensional Arrays in Polymer Nanocompositites", Advanced Materials, vol. 11, No. 3, pp. 231-234 (1999).

(56) References Cited

OTHER PUBLICATIONS

Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).
Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).
Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).
LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).
Lagerholm et al., "Theory for Ligand Rebinding at Cell Membrane Surfaces," Biophysical Journal (1998), vol. 74, pp. 1215-1228.
Lamb, D. J., et al., "Modification of Natural and Artificial Polymer Colloids by Topology-Controlled Emulsion Polymerization". Biomacromolecules, vol. 2, No. 2, pp. 518-525 (2001).
Lander, E. S. "The New Genomics: Global Views of Biology". Sciences, vol. 274, No. 5287, pp. 536-539 (Oct. 25, 1996).
Lander, E. S., et al., "Array of Hope". Nature Genetics Supplement, Perspective, vol. 21, pp. 3-4, (Jan. 1999).
Latour, P., et al., "Polymorphic Short Tandem Repeats for Diagnosis of the Charot-Marie-Tooth IA Duplication". Clinical Chemistry, vol. 47, pp. 829-837 (2001).
Lau, F. Y., et al., "Provision of phenotype-matched blood units: no need for pre-transfusion antibody screening", Haematologica, vol. 86, No. 7, Jul. 2001, pp. 742-748.
Lee et al. "Quantitation of residual WBCs in filtered blood components by high-throughput, real time kinetic PCR", Blood Components, transfusion, vol. 42, pp. 87-93 (Jan. 2002).
Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).
Lee, H. J., et al., "Fabricating RNA Microarrays with RNA-DNA Surface Ligation Chemistry". Analytical Chemistry, vol. 77, No. 23, pp. 7832-7837 (Dec. 1, 2005).
Lee, S., et al., "Control of Core-Shell Latex Morphology". Polymer Latexes, ACS Symposium, American Chemical Society, pp. 234-253 (1992).
Lemieux: "high throughput single nucleotide polymorphism genotyping technology" Current Genomics. vol. 1:301-311 (2000).
Lhomme et al. "Abasic DNA structure, reactivity and recognition". Biopolymers. vol. 52 : 65-83 (1999).
Li, A., et al., "Multiplexed analysis of polymorphisms in the HLA gene complex using bead array chips". Tissue Anitigens, vol. 63, pp. 518-528 (2004).
Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).
Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235-246 (1999).
Liebert, M. R., et al., "Dynamics of the holes in human erythrocyte membrane ghosts". J. Biological Chemistry, vol. 257, No. 19, pp. 11660-11666 (1982).
Lin et al. "Raman Studies of Bovine Serum Albumin" . Biopolymers 15:203-218 (1976).
Lindahl et al., "Rate of depuriniation of native deoxyribonucleic acid". Biochemistry. vol. 11, No. 19: 3610-1617 (1972).
Lindahl et al., "Rate of chain breakage at apurinic sites in double-stranded deoxyribonclueic acid" Biochemistry, vol. 11, No. 19:3618-3623 (1972).

Lipshutz, R. J., et al., "High Density Synthetic Oligonucleotide Arrays". vol. 21, pp. 20-24 (Jan. 1999).
Liu, et al., "Development of a Carbon Dioxide-Base Microencapsulation Technique for Aqueous and Ethanol-Based Lateses". Langmuir (2002).
Liu, V, et al, "Three-Dimensional Photopatterning of Hydrogels Containing Living Cell". Biomedical Microdevices, vol. 4, No. 4, pp. 257-266 (2002).
Lofas, et al., "Methods for site controlled coupling to carboxymethyldextran surfaces in surface plasmon resonance sensors". Biosensors & Bioelectronics, vol. 10, pp. 813-822 (1995).
Loomans, E., et al., "Assessment of the functional affinity constant of monoclonal antibodies using an improved enzyme-linked immunosorbent assay". Journal of Immunological Methods, vol. 184, pp. 207-217 (1995).
Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).
Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).
Luo et al., "Emulsion Copolymerization of Butyl Acrylate with Cationic Monomer Using Interfacial Redox Initiator System". Journal of Polymer Science, vol. 39, pp. 2696-2709 (2001).
Lvov, Y, et al., "Alernate Assembly of Ordered Multilayers of SiO2 and Other Nanoparticles and Polyions". Langmuir, vol. 13, pp. 6195-6203 (1997).
Maldonado-Rodriguez et al., "Hybridization of glass-tethered oligonucleotide probes to . . . ", Molecular Biotechnology, vol. 11, No. 1, pp. 1-12 (1999).
Marras et al., Multiplex detection of single-nucleotide variations using molecular beacons: Genetic Analysis: Biomolecular Engineering 14 (1999) 151-156.
Martin, M., et al. "A Method for Using Serum or Plasma as a Source of DNA for HLA Typing". Human Immunology, vol. 33, pp. 108-113 (1992).
Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.
Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).
Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).
Matthews et al., "Biochemistry: A Short Course". New York: John Wiley & Sons, Inc, p. 25 (1997).
Maxam et al., "A new method for sequencing DNA," Proc. Natl. Acad. Sci. USA. vol. 74, No. 2, pp. 560-564, Feb. 1977.
McCloskey, et al., "Magnetic Cell Separation: Characterization of Magnetophoretic Mobility". Anal. Chem., vol. 75, pp. 6868-6874 (2003).
McCloskey, et al., "Magnetophoretic Mobilities Correlate to Antibody Binidng Capacities". Cytometry, vol. 40, pp. 307-315 (2000).
Mei et al. "Genome-wide Detection of Allelic Imbalance Using Human SNPs and High-Density DNA Arrays". Genome Research. vol. 10, pp. 1126-1137 (2000).
Michael, et al., "Randomly ordered addressable high-density optical ssensor arrays". Anal. Chem, vol. 70, pp. 1242-1248 (1999).
Micheletto et al., "A simple method for the production of a two-dimensional ordered array of small latex particles". Langmuir, vol. 11, pp. 3333-3336 (1995).
Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).

(56) References Cited

OTHER PUBLICATIONS

Moore, et al., "The use of magnetite-doped polymeric microspheres in calibrating cell tracking velocimetry". J. Biochem. Biophys. Methods, vol. 44, pp. 115-130 (2000).

Morag et al. "Immobilized nitro-avidin and nitro-streptavidin as reusable affinity matrices for application in avidin-biotin technology". Analytical Biochemistry. vol. 243: 257-263 (1996).

Mori, et al., Computer program to predict liklihood of finding an HLA-matched donor: Methodology, validation, and application. Biology of Blood and Marrow Transplantation, vol. 2, pp. 134-144 (1996).

Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.

Muller et al., "Gene and Haplotype Frequencies for the Loci HLA-A, HLB-B, and HLA-DR Based on Over 13,000 German Blood Donors". Human Immunology, 2003, 64: 137-151.

Mullis et al. Specific Synthesis of DNA in Vitro via a Polymerase-Catalyzed Chain Reaction Methods in Enzymology, 1987; vol. 155, pp. 335-350.

Nagarajan et al., "Identifying Spots in Microarray Images", IEEE Transactions on Nanobioscience, vol. 1, No. 2, pp. 78-84 (Jun. 2002).

Nagayama et al., "Fabrication of two-dimensional colloidal arrays". Phase Transitions, vol. 45, 185-203 (1993).

Nam, J., et a., "Colorimetric Bio-Barcode Amplification Assay for Cytokines". Anal. Chem., vol. 77, pp. 6985-6988 (2005).

Nau et al., "A Command Processor for the Determination of Specificities fro Matrices of Reactions Between Blood Cells and Antisera". Computers and Biomedical Research, vol. 10, pp. 259-269 (1977).

Nazarenko et al. (2002) Multiplexed quantitiative PCR using self-quenched primers labeled with a single fluorophore, Nucleic Acids Research, 30 (9), e37.

Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).

Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).

Nygren, "Molecular Diagnostics of Infectious Diseases" Royal Institute of Technology Department of Biotechnology, Stockholm 2000, pp. 1-68.

Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.

Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo et al., "Preparation of micron-size monodisperse polymer particles by seeded polymerization utilizing the dynamic monomer swelling method". Colloid and Polymer Science, vol. 269, No. 3, pp. 222-226 (1991).

Olejnik et al., "Photocleavable biotin phosphoramidite for 5'-end-labeling, purification & phosphorylation of oligonucleotides", Nucleic Acids Research 1996, vol. 24, 2:361-366.

Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).

Olson et al. "A common langauage for physical mapping of the human genome". Science, vol. 245, pp. 1434-1435 (1989).

Otero, T. F., et al., "Electrochemically initiated acrylic acid/acrylamide copolymerization", J. Electroanal. Chem., vol. 256, pp. 433-439 (1998).

Otero, T. F., et al., "Electroinitiated polymerization of acrylamide in DMG: Attempts at an interfacial model", J. Electroanal. Chem., vol. 304, pp. 153-170 (1991).

Pastinen, et al., "A System for specific, high-throughput genotyping by allele-specific primer extension on microarrays". Genome Res., vol. 10, pp. 1031-1042 (2000).

Peter, C., et al., "Optical DNA-sensor chip for real-time detection of hybridization events". Fresenius J. Anal. Chem, vol. 371, pp. 120-127 (Jun. 2001); Published online Springer-Verlay 2001.

Wilson, M. R., et al., "A New Microsphere-based Immunofluorescence Assay for Antibodies to Membrane-associated Antigens". Journal of Immunological Methods, vol. 107, pp. 231-237 (1988).

Peterson, et al. "Fiber Optic pH probe for physiological use". Anal. Chem. vol. 52, 864-869 (1980).

Peterson, et al., "Fiber Optic Sensors for Biomedical Applications". Science, vol. 13; pp. 123-127 (1984).

Peytavi et al., "Correlation between microarray DNA hybridization efficiency and the position of short capture probe on the target nucleic acid". Biotechniques, vol. 39, No. 1, pp. 89-96 (2005).

Pooga, M., et al., "Cell-Penetrating constructs regulate galanin receptor levels and modify pain transmission in vivo" Nature Biotechnology, vol. 16, pp. 857-861 (1998).

Pope. "Fiber optic chemical microsensors employing optically active silica microspheres". SPIE, vol. 2388; pp. 245-256 (1995).

Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.

Pregibon et al, "Magnetically and Biologically Active Bead-Patterned Hydrogels". Langmuir, vol. 22, pp. 5122-5128 (2006).

Preza, "Phase Estimation using rotational diversity for differential interference contrast microscopy". Dissertation presented to the Washington University, Server Institute of Technology, Department of Electrical Engineering; St. Louis, MO (Aug. 1998).

Proudinikov et al., "Chemical methods of DNA and RNA fluorescent labeling". Nucleic Acids Research. vol. 24, No. 22: 4535-4542 (1996).

Proudnikov , D., et al., "Immobilization of DNA in Polyacrimide Gel for the Manufacture of DNA and DNA-Oligonucleotide Microchips", Analytical Biochemistry, vol. 259, pp. 34-41 (1998).

Quon, R., et al., "Measurement of the Deformation and Adhesion of Rough Solids in Contact". J. Phys. Chem., vol. 103, pp. 5320-5327 (1999).

Rabbany et al., "Assessment of hetrogeneity in antibody displacement reactions". Anal Chem, vol. 69, pp. 175-182 (1997).

Radtchecnko et al., "Core-shell structures formed by the solvent-controlled precipitation of luminescent ScTe nanocrystals on latex spheres". Advanced Materials, vol. 13, No. 22, pp. 1684-1687 (2001).

Radtkey et al., "Rapid, high-fidelity analysis of simple sequence repeats on an electronically active DNA microchip". Nucleic Acids Research, vol. 28, No. 7, p. e17 (2000).

Ramsay, G., "DNA Chips: State-of-the-Art". Nature Biotechnology, vol. 16, pp. 40-44 (Jan. 1998).

Reddy et al., "Determination of the Magnetic Susceptibility of Labeled Particles by Video Imaging". Chemical Engineering Science, vol. 51, No. 6, pp. 947-956 (1996).

Reid M.E., et al., "Novel Dombrock blood group genetic variants . . . ", Blood (ASH Annual Meeting Abstract) 2004, 104: Abstract 383.

Relogio, A. et al., "Optimization of oligonucleotide-based DNA microarrays", Nucl. Acids Res., vol. 30, e51, pp. 1-10 (2002).

Richardson et al., "The use of coated paramagnetic particles as a physical label in a magneto-immunassay". Biosensors & Bioelectronics, vol. 16, pp. 989-993 (2001).

Richardson, et al., "A novel measuring system for the determination of paramagnetic particle lables for use in magneto-immunoassays". Biosensors & Bioelectronics, vol. 16, pp. 1127-1132 (2001).

(56) References Cited

OTHER PUBLICATIONS

Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).
Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al., "Precipitation with Ethanol or Isopropanol", Concentrating Nucleic Aicds, Molecular Cloning vol. 3, pp. E3-E4 and E.10-E.15 (1989).
Sano, T, et al., "Immuno-PCR: Very Senisitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when Linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al., "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).
Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).
Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).
Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262 : 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham , P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).
Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).

(56) References Cited

OTHER PUBLICATIONS

Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvilli, S.A. et al. "Adsorption of human serum albumin: Dependence on molecular architecture of the oppositely charged surface" J. Chem, Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucelotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genone-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly-(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).
Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells", Malaria Journal (2004) pp. 1-7 from http://www.malari-ajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).

Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". vol. 125, No. 26, pp. 7798-7799, (Jul. 2, 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).
Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry. vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., "Working Party of the BCSH: Guidelines for compatibility procedures in blood transfusion laboratories", Transfusion Medicine, vol. 14, pp. 59-73 (2004).
Yamashita et al., "Thermodynamics for the preparation of micron-sized, monodispersed highly monomer absorbed polymer particles utilizing the dynamic selling method". Colloids and Surfaces, vol. 153, pp. 153-159 (1999).
Yao et al., "Molecular-beacon-based array for sensitive DNA analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).
Hermanson, Greg T., "Zero Length Cross-Linkers"; Bioconjugate Techniques; Academic Press, pp. 170-176 (1996).
Hermanson, Greg T., "Bioconjugate Techniques", Bioconjugate Techniques; Academic Press, San Diego, 430-33, (1996).
MacBeath et al., "Printing proteins as microarrays for high-throughput function determination," Science vol. 289: 1760-1763 (2000).
Tobitani et al. "Heat-induced gelation of globular proteins 2. Effect of environmental factors on single-component and mixed-protein gels," Macromolecules; vol. 30: 4855-4862 (1997).
Wittemann et al., "Interaction of Proteins with Spherical Polyelectrolyte Brushes" (Polyer Institute, University of Karisruhe, Karisruhe, Germany) Poster Oct. 2001.
Brick et al., "Formation of Colloidal Dispersions of Organic Materials in Aqueous Media by Solvent Shifting". *Langmuir*, vol. 19, No. 16, pp. 6367-6380 (2003).

(56) References Cited

OTHER PUBLICATIONS

Friedli, "Interaction of SWP with Bovine Serum Albumin (BSA) and Soluble Wheat Protein" (SWP) (7 pages) downloaded http://www.friedli.com/research/PhD/chapter5a.html (1997).

Giersig et al. Formation of ordered two-dimensional gold colloid lattices by electrophoretic deposition. *J. Phys. Chem.*, vol. 97, No. 24, 6334-6336 (1993).

Hermanson, G. T., "Nucleic Acid and Oligonucleotide Modification and Conjugation." *Bioconjugate Techniques, Academic Press*, Chapter 17, pp. 639-671 (Jan. 15, 1996).

MacBeath et al., "Printing proteins as microarrays for high-throughput function determination." *Science*, vol. 289; pp. 1760-1763 (2000).

Marsh et al., The HLA Facts Book, "HLA Typing at the DNA Level", Academic Press, Chapter 6, pp. 37-39 (2000).

\* cited by examiner

Flip gel with exposed microparticles

Assay Format

Assay Result

Assay Format

Assay result

UN-SUPPORTED POLYMERIC FILM WITH EMBEDDED MICROBEADS

CROSS-REFERENCE TO RELATED APPLICATION

This application is a continuation of Ser. No. 10/034,727, filed on Dec. 12, 2001 now U.S. Pat. No. 7,262,063, which claims priority to Provisional Application No. 60/300,025, filed Jun. 21, 2001. Priority to both these applications is hereby claimed.

BACKGROUND OF THE INVENTION

A longstanding objective within the materials, engineering, biomedical and analytical sciences has been the design of ever-smaller structures and devices for use in miniaturize systems capable of performing specific functions, such as sensors, transducers, signal processors or computers. Of particular interest as potential building blocks in this context have been functional materials having predetermined properties. Patterned films composed of suitable polymers and polymer-microparticle composite films offer particularly attractive opportunities to realize hierarchically organized structures of functional materials and to provide confinement and segregation for performing "local" chemical reactions.

Several methods of preparing patterned polymer films and polymer-microparticle composite films have been described. In one example, polymer molding has been used to prepare polymeric films. Beginning with a master that is fabricated from a silicon (Si) wafer using conventional lithographic techniques, a mold is made using an elastomer such as polydimethylsiloxane (PDMS). The mold is then used to produce replicas in a UV-curable polymer such as polyurethane. The applicability of this technique of polymer molding, long used for replication of micron-sized structures in devices such as diffraction gratings, compact disks, etc., recently has been extended to nanoscale replication (Xia, Y. et al., Adv. Mater. 9:147 (1997), Jackman, R. J. et al., Langmuir. 15:2973 (1999), Kim, E. et al. Nature 376, 581 (1999).

Photolithography has been used to produce patterned, stimuli-sensitive polymeric films which can be further functionalized with bioactive molecules and which undergo abrupt changes in volume in response to changes in pH and temperature (Chen, G. et al., Langmuir. 14:6610 (1998); Ito, Y. et al., Langmuir 13:2756 (1997)). UV-induced patterned polymerization of various hydrogel structures within microchannels has been described as a means for the autonomous control of local flow (Beebe, D. J. et al., Nature. 404:588 (2000)).

Surface-initiated ring-opening metathesis polymerization following microcontact printing has been used to create patterned polymer layers which remain attached to the surface and produce structures of controlled vertical and lateral dimensions (Jeon, N. L. et al., Appl. Phys. Lett. 75:4201 (1999)). Other techniques such as thermal radical polymerization (Liang, L., J. Appl. Polym. Sci. 72:1, (1999)) and UV-induced polymerization (Liang, L., J. Membr. Sci. 162:235 (1999)) have been used to generate surface confined thin, uniform and stimuli-sensitive polymeric films.

Sarasola, J. M. et al. (J. Electroanal. Chem. 256:433, (1988) and Otero, T. F. et al., J. Electroanal. Chem. 304:153, (1991) describe electropolymerization of acrylamide gels using Faradaic process. Acrylaminde gels are prepared on electrode surfaces by an anodic oxidative polymerization process using the electroactive nature of acrylamide monomers.

Polymerization of crosslinked acrylamide has been described to produce a matrix of glass-immobilized polyacrylamide pads which were activated with receptor molecules of interest including oligonucleotides or proteins. The use of the resulting porous and highly hydrated matrix for simultaneous monitoring of ligand-receptor binding reactions has been reported (Proudnikov, D. et al., Anal. Biochem. 259:34 (1998); Yershov, G., Proc. Natl. Acad. Sci. U.S.A. 93:4913 (1996), LaForge, S. K., Am. J. Med. Genet. 96:604 (2000); Khrapko, K. R. et al. U.S. Pat. No. 5,552,270, 1996; Ershov, G. M. et al. U.S. Pat. No. 5,770,721, 1998; Mirzabekov et al. U.S. Pat. No. 6,143,499.).

A process for the assembly of a 3-D array of particles has been described which is based on the synthesis of a coreshell latex particle containing a core polymer with a glass transition temperature significantly higher than that of the shell polymer. In accordance with that process, particles were assembled into a 3-D close packed structure and annealed in such a way that the core particle remained unaltered while the shell polymer flowed, resulting in a continuous matrix embedding an organized 3-D array of core particles (Kalinina, O. and Kumacheva, E., Macromolecules. 32:4122 (1999); Kumacheva, E. et al., Adv. Mater. 11:231 (1999), Kumacheva, E. et al., U.S. Pat. No. 5,592, 131 (1999)).

The encapsulation of a colloidal crystalline array within a thin, environmentally sensitive hydrogel matrix capable of swelling in response to changes in pH and temperature has been described. In other instances, the hydrogel contained immobilized moieties capable of triggering the swelling of the gel in the presence of particular analytes. The swelling of the gel matrix increases the periodicity of the colloidal crystal array and produces a shift in Bragg diffraction peaks in the spectra of the scattered light (Holtz, J. H. et al., Anal. Chem. 70:780 (1998); Haacke, G. et al., U.S. Pat. No. 5,266,238, 1993; Asher, S. A., U.S. Pat. No. 5,281,370, 1994). The process of forming the colloid crystal relies on passive diffusive transport of particles within the prepolymer reactive mixture.

Each of the aforementioned references are incorporated herein by reference in its entirety.

SUMMARY OF THE INVENTION

The present invention provides a systemic synthetic process to translate a sequence of synthetic instructions into a sequence of synthetic operations that are performed in a homogenous fluid phase, to produce patterned polymeric films, functional polymeric films, multicomponent microparticle assemblies and/or polymer-microparticle film composites of pre-determined composition, layout and morphology. Rather than arranging individual molecules by explicit external placement, this approach combines dynamically controlled "self-assembly" and triggered polymerization process to realize heterostructures of pre-conceived architecture and design.

In one aspect, the present invention provides methods and apparatus for assembling particles at preset times and in predesignated positions on a substrate surface and to mediate the transformation of thin, patterned gel films. The present invention thus permits a sequence of multiple reaction steps to be executed at preset times in accordance with an externally set schedules within a homogenous reaction, each step invoking an active transport or reaction process.

In another aspect, the present invention provides processes and apparatus for synthesis of patterned polymer films and/or polymer-microparticle film composites that are mediated by AC electric field. The present invention also relates to the incorporation of the gels and composites into other structures. The present invention further relates to the application of such gels and composites in material science and biology. Illustrative areas of application include: catalysts, smart materials, membranes, sensors and microreactors.

In contrast to some of the methods for producing functionalized polymeric films, the present invention does not require complex chemistries of limited applicability nor does it require multiple unrelated processing steps. Furthermore, in the case of polymer-microparticle film composite structures, the present invention does not rely on diffusive transport, a slow and environmentally sensitive process, in the assembly of ordered particle arrays.

DETAILED DESCRIPTION OF THE INVENTION

Figure 1:
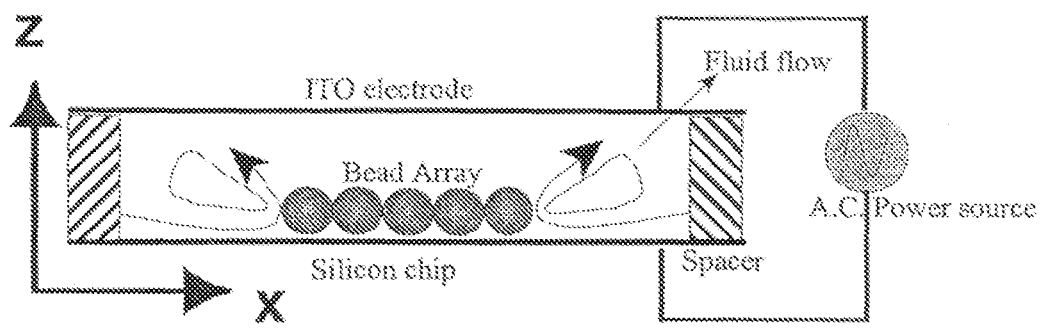
FIG. 1 is an illustration showing an experimental configuration for LEAPS.

The present invention provides methods for synthesis of patterned polymeric films and/or polymer-microparticle film composites that are simple in implementation and flexible in the choice of polymer chemistry used. Also provided is an apparatus useful in said methods. Patterned polymer films and polymer-microparticle film composites and their uses are also provided. The invention is based at least in part on the technology designated "LEAPS" (which refers to "Light-Controlled Electrokinetic Assembly of Particles near Surfaces).

In certain embodiments, the methods of the present invention combines the action of an active self-assembly process acting on long length scales such as LEAPS with externally triggered, template-directed gel chemistries to provide: the self-assembly of microparticle arrays in designated positions on a planar or substantially planar substrate, the externally directed, sequential execution of multiple assembly steps requiring a schedule of initiation and termination; and spatial confinement to enable concurrent execution of multiple assembly steps in different compartments. The resulting heterostructures exhibit an organization in accordance with a predesigned architecture to meet the requirements associated with the execution of specific functions. Applications of the process to the fabrication of functional materials, sensors and more generally chemical transducers and information processors also are of interest.

Light-Controlled Electrokinetic Assembly of Particles Near Surfaces

LEAPS technology relates to movement of particles and/or fluid suspended at an electrolyte solution-electrode interface and is described in detail in PCT International Application No. PCT/US97/08159 and U.S. Pat. No., as well as in U.S. Ser. No. 09/397,793, filed Sep. 17, 1999; U.S. Ser. No. 09/320,274, filed May 28, 1999, and PCT International Application No. PCT/US00/14957; U.S. Ser. No. 09/813,571, filed Mar. 21, 2001; and PCT International Application No. PCT/US01/20179, filed Jun. 21, 2001. Each of these patents/patent applications is incorporated by reference in their entirety.

LEAPS involves the use of electrokinetic and polarization-induced forces which arise in accordance with the lateral impedance gradients at an interface between an electrolyte solution and an electrode to control fluid flow, particle transport and/or particle assembly.

In one embodiment of LEAPS, a plurality of particles are suspended in an interface between an electrolyte solution and a light sensitive electrode (e.g., a planar electrode). An AC electric field is generated at the interface and the interface is illuminated with a predetermined light pattern to assemble particles in the areas of the electrode designated by the pattern of illumination (e.g., regions of low impedance). Particles move to the low impedance area and form an assembly when the frequence of the applied electric field is less than the relaxation frequency of the particles. Accordingly, if the relaxation frequency of the particles are known, one can directly adjust the frequency of the electric field to form the particle assembly. If the relaxation frequency of the particles are not known, then the frequency of the applied AC field may be readily adjusted until the assembly occurs. If no particles are present in the interface, and the movement of the fluid is what is desired, that may be accomplished by adjusting the frequency of the applied electric field to be less than the relaxation frequency of the electrolyte solution-electrode interface.

In another embodiment of LEAPS, a patterned electrode is used instead of the light-sensitive electrode. For example, a first electrode is positioned in a first plane and a second electrode (preferably of planar geometry) is positioned in a second plane different from the first. The particles suspended in an electrolyte solution (or an electrolyte solution without the particles) are located between the first and the second electrode. The second electrode comprises a patterned electrode. The term "patterned electrode," as used herein, refers to an electrode having a surface and an interior, either or both of which are modified to produce spatial modulations in the properties of the second electrode that affects the local distribution of the electric field at the electrolyte solution-electrode interface. When the AC electric field is applied at the interface, the particles assemble in designated areas of the second electrode that are defined by the spatial modulations in the properties of that electrode (e.g., low impedance regions). In the absence of the particles, fluid movement may also be controlled by the application of AC field.

The electrode may patterned by a number of ways to affect the interfacial impedance. Preferably, the electrode is patterned by spatially modulated oxide growth, surface chemical patterning or surface profiling. If the patterned electrode is a light-sensitive electrode, the patterning in combination with the illumination pattern on said electrode may be used to control the movement of the particles and/or fluid at the solid-liquid interface.

In preferred embodiments, the patterned or light-sensitive electrode comprises a silicon electrode (e.g., silicon chip), which may also be coated with a dielectric layer. One such example is a Si/SiOx electrode. In one particularly preferred LEAPS configuration, an additional electrode is provided such that the light-sensitive (or the patterned electrode) and the additional electrode are substantially planar and parallel to one another and separated by a gap (e.g., in a sandwich configuration), with the electrolyte solution (with or without the particles) being located in the gap. The additional electrode preferably comprises an optically transparent electrode (e.g., ITO coated glass), which allows optical inspection of the movement of the particles and/or fluid at the interface. When such type of LEAPS cell is used, an AC electric field may be applied at the solid-liquid interface by applying an AC voltage between the light-sensitive (or patterned) electrode and the additional electrode.

When a plurality of particles are suspended in the electrolyte solution and subject to LEAPS, it is preferred that the particles form a planar assembly on the designated areas of the electrode, more preferably in an array configuration. However, the particles may also be assembled in a linear configuration or any other configuration that is dictated by the illumination pattern and/or patterning.

The term "particles" as used herein include colloidal particles, eukaryotic and prokaryotic cells, micells, vesicles (e.g., liposomes) and emulsion droplets. In preferred embodiment, the size of the particles range from about 0.2 to about 20 µm in diameter.

Formation of Patterned Polymeric Film

The present invention provides methods for synthesizing patterned polymeric film using the LEAPs technology described in the preceding section. In certain embodiments, a polymerization mixture comprising a monomer and an initiator in an electrolyte solution is provided. Preferably, the polymerization mixture also contains a cross-linker, with the monomer, initiator and the crosslinker dissolved in the electrolyte solution. This mixture is placed between the light-sensitive (or patterned) electrode and the additional electrode. An AC electric field is applied in the interface between the electrolyte solution and the light-sensitive (or patterned) electrode. Lateral impedance gradients at the interface, set up by the patterning or the predetermined pattern of illumination, give rise to local recirculating electro-osmotic fluid motion, which effectively transports fluid (and particles if they are present) from regions of high impedance to regions of low impedance. Depending on the initiators used, the application of the AC electric field, in addition to the illumination of the electrode with a predetermined light pattern (when light-sensitive electrode is used) or the patterning of the electrode, may be sufficient to induce formation of a patterned polymeric film on the low impedance regions of the light-sensitive or patterned electrode.

In preferred embodiments, the polymerization is triggered at a desired time by using initiators that are heat or photo-activated. If such a case, the polymerization mixture is heated or irradiated with UV-light to initiate polymerization. Heat-generated or UV-generated free radicals diffuse and react with monomers to produce initially oligomers and finally a crosslinked polymer film.

As the gel film grows, a moving reaction extends into the solution with time. In case of the heat-induced polymerization, polymerization starts from the light-sensitive or patterned electrode (e.g., silicon chip). Due to the presence of LEAPs-mediated, strong convective transport near the light-sensitive (or patterned) electrode surface, the polymerization process is triggered preferentially in the low impedance areas on that electrode, thereby giving rise to a spatially patterned polymeric film on said electrode. In case of UV-induced polymerization, however, polymerization starts at the additional electrode (usually the top electrode), and produces an unpatterned monolithic gel.

The present invention, in contrast to several known methods, do not require complex implementation, such as use of a mask, in preparation of patterned gel films. In addition, the methods of the present invention allow increased flexibility in choice of monomers, crosslinkers and initiators used. It should, however, be noted that high viscosity of the polymerization mixture and high ionic concentration may impede with the proper functioning of LEAPS by interfering with the interfacial fluid flow. Accordingly, it is recommended that the ionic concentration of the polymerization mixture be about 1.0 mM or lower, preferably between about 0.1 mM to 1.0 mM. This may be accomplished by selecting initiators to maintain low ionic concentration of the mixture. Initiators, as are monomers and crosslinkers, are well known in the art and may readily be obtained from commercial sources.

As for the monomers and crosslinkers, it is recommended that low viscosity monomers and crosslinkers be used, such that the viscosity of the polymerization mixture is about 100 cp or less. When the patterned film to be produced is a hydrogel, water-soluble monomers are preferred. In addition, when said film is optically transparent. The desired monomer concentration may be adjusted according to the type of gel to be produced (e.g., self-supporting or cleaved gel). In one embodiment, a mixture of acylamide and bisacrylamide of varying monomer concentrations, from about 20% to about 5%. (acylamide:bisacrylamide=37.5:1, molar ratio) may be used to produce a hydrogel. In preferred embodiments, the polymeric film obtained comprises a cross-linked alkylacrylamide or hydroxyalkymethacrylate hydrogel.

The AC voltage depends on the polymerization mixture and is readily adjusted until the desired polymeric film (or polymer-microparticle film composite) is formed. Preferably, the voltage applied is in the range of about 0.5 to about 15 V (peak to bead) and the frequency is preferably more than about 10 hz and less than about 500 kHz, more preferably about 1 kHz to 10 kHz.

In one embodiment of the invention, LEAPS is carried out in a fluidic microcell formed by sandwiching a double-sided Kapton spacer of about 100 um thickness (between a 1 cm×1 cm silicon chip (n-typed, capped either by a uniform or a lithographically patterned thin SiO2 layer) and a glass cover slip coated with indium tin oxide (ITO) to a typical sheet resistance of 1400 Ohn square.

In preferred embodiments of the present invention, an electrolyte solution (more preferably, an aqueous solution) is used in the polymerization mixture, e.g., to dissolve monomers, crosslinkers and initiators. In certain embodiments, other polarizable liquid medium may be used, including non-aqueous solution. The relaxation frequency of the particles assembled in a non-aqueous solution (e.g., DMSO and acetonitrile) is shifted to lower values when compared with that of an aqueous solution.

The hydrogels of the present invention may be functionalized by variety of methods known in the art. For example, during the polymerization step itself small amounts of functional monomers may be introduced along with the polymerization mixture (e.g., acrylamide mixture). Acrylic acid, 2-hydroxyethylmethacrylate (HEMA), diethylaminoethylmethacrylate hydrochloride etc. could be incorporated into the hydrogel so that the micropatterned gel may be chemically addressed via the carboxy, hydroxy and amino functional groups. Biomolecules of interest may subsequently be immobilized in the gel using suitable chemistry and linker molecules.

Small probe molecules or functional co-monomers may also be introduced into the hydrogel using the same approach to yield novel sensor and stimuli responsive hydrogel structures, that can respond to a variety of inputs such a pH, temperature, electric field, light etc. Microscale structures made from such stimuli-responsive materials may act as an actuator, for example for controlling fluid flow (valve). Such structures will be self regulating and would not require an external power source.

Polymer-Microparticle Film Composites

By providing a plurality of particles suspended in the polymerization mixture, the methods for patterned polymeric film synthesis, as described in the preceding section, may be used to obtain an assembly of the particles embedded in a polymeric film (also referred to as "polymer-microparticle composite" or "heterostructure"). The composite formation is comprised of two stages. First, particle assemblies (e.g., planar particle assemblies, more preferably particle arrays) are formed from the particle suspension also containing all ingredients required for subsequent in-situ gel formation, as described previously. Second, a polymeric film is formed to produce the polymer-microparticle film composite. In one preferred embodiment, gels are formed by heat-initiated in-situ polymeriation to form a composite in which the gels are spatially patterned. In another preferred embodiment, the gels are formed by UV-initiated in-situ polymeriation to obtain a composite in which the gels are monolithic (not patterned).

In one embodiment, AC voltage of 1 to 20 V p-p in a frequency range of from about 100's of hertz to several kilohertz are applied between the electrodes across the fluid gap. Fluid and particle transport and assembly may be monitored by video microscopy permitting frame capture and digitation of frames for further analysis.

The thermal free radical polymerization may be initiated by heating the polymerization mixture (e.g., by heating the LEAPs cell), for example, to about 40 to 45 C, for about 1 to 10 minutes, using an IR lamp, while maintaining the AC electric field at the electrolyte solution-electrode interface, to form a patterned film or polymer-microparticle film composite.

The polymerization may also be triggered by irradiating the polymerization mixture with UV-light. For example, in the presence of the applied AC electric field, polymerization may be triggered by using a mercury lamp source. A wide range of wavelengths spanning from about 250 to 340 nm may be used, for about 15 seconds to about 10 minutes. In one preferred embodiment, the concentration of monmers in the polymerization mixture may be about 10% by weight, and 2-hydroxy-4'-hydroxyethoxy-2-methylpropiophenoe) may be used as the initiator to give a 1.5% by weight solution.

In certain embodiments, particles comprise beads (also referred to as "microparticles" or "microspheres") that are composed of silica, modified polystyrene or other polymers. Preferably, these particles are anionic or cationic particles ranging from about 0.5 μm to about 15 μm in diameter. In certain preferred embodiments, these particles are functionalized by attaching a variety of chemical functional groups to their surfaces. The process of forming composite gel-particle films may readily be extended to particles that display biomolecules attached on their surfaces, such as receptors or ligands. In certain embodiments, oligopeptides, proteins, oligonucleotides or nucleic acid fragments may also be attached to the particle surfaces. The particles may also be encoded by use of a chemically or physically distinguishable characteristic that are uniquely identifies the biomolecules attached to those particles, an example of which includes color encoding the particles using flourophore or chromophore dyes. Such a process allows chemical immobilization of functionalized microparticle assemblies or arrays for a variety of biochemical assays, including binding and functional assays. Examples 6 to 9 describe a number of these assays.

In certain embodiments, the particles used in preparing polymer-microparticle film composites may be magnetic particles. In certain other embodiments, the particles used are eukaryotic or prokaryotic cells, or liposomes. The polymer-microparticle film composites produced using these particles may also be used in various biochemically assays, including the assays described in Examples 12 to 16.

The particles useful in preparation of the polymer-particle film composite may also comprise inorganic particles, including metal particles, semiconductor particles and glass particles. The inorganic particles may also be coated with a polymeric shell.

Self-Supporting, Flipped and Cleaved Gels and Gel-Microparticle Films

Accordingly, the present invention provides novel patterned films and/or polymer-microparticle film composites, including a planar assembly or array of particles embedded in a gel (2-dimensional assembly). In preferred embodiment, these gels are prepared according to the methods described above.

As discussed previously, the patterned polymeric films and the polymer-microparticle film composites of various types may be produced, for example, by varying the monomer concentration.

In one embodiment of the present invention, a self-supporting film (preferably a hydrogel) is prepared. In one example, the concentration of monomers in the polymerization is greater than about 10% by weight. Preferably, acrylamide monomers are used. Following the polymerization, the LEAPS microcell may be dismantled with the gel matrix attached to the light-sensitive (or patterned) electrode. The hydrogel produced is self supporting and free standing patterned gel films may be obtained simply by peeling it off from the electrode. The film is stable in aqueous solution and stays intact for months. An example of such a free standing gel is shown in FIG. 2(b).

In addition to the substrate-supported and self-supporting gel films described above, a "Lift-Off" processes may be used to obtain polymeric films and/or composites that are detached from the light-sensitive (or patterned) bottom electrode. In one example, a vinyl siloxane coated ITO coverslip is used as an electrode for the LEAPS assembly cell. The vinyl siloxane coating allows covalent tethering of the gel film on the ITO electrode. Beads, suspended in a solution containing all ingredients required for subsequent in-situ gel formation, are assembled in designated regions of the light-sensitive (or patterned) electrode using an AC-electric field at a given voltage and frequency.

Figure 4A:
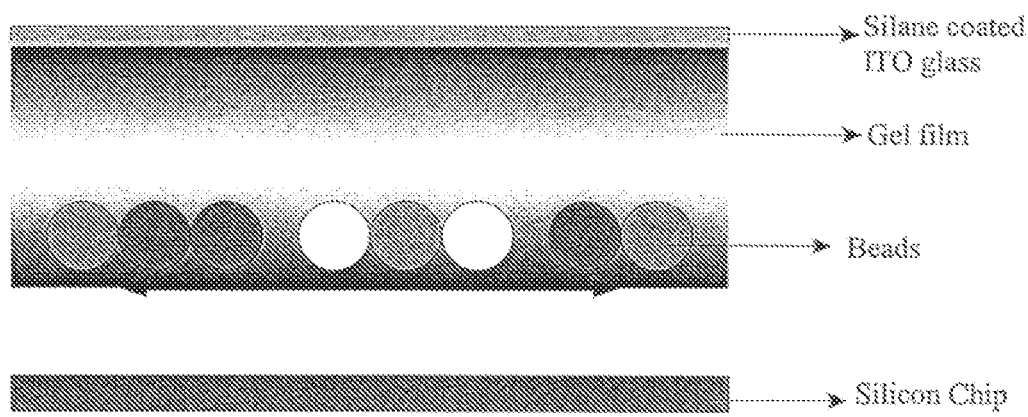
FIG. 4(a) is an illustration showing a flipped gel-particle composite film.

Keeping the field switched on, the LEAPs cell may, for instance, be irradiated with UV-light from a 150W Hg source for ~3 minutes. Afterwards, the UV illumination and field are switched off and the LEAPS cell is opened by separating the bottom silicon electrode from the top ITO electrode: the covalent attachment of the gel to the top electrode ensures that the gel remains adhered to the top electrode and readily separates from the bottom electrode. By "flipping" the substrate-attached gel film, beads displaying receptors capable of binding the molecules of interest are located at the outer, exposed surface of this "flipped" gel ("FlipGel"). Thus, the diffusion length of the molecules to migrate from the solution above the gel to the bead surface is small compared to that in the case of regular gels (see FIG. 4(a)). An assay is then conducted on the gel-embedded bead array by exposing the gel to the solution containing analyte molecules of interest.

Figure 4B:
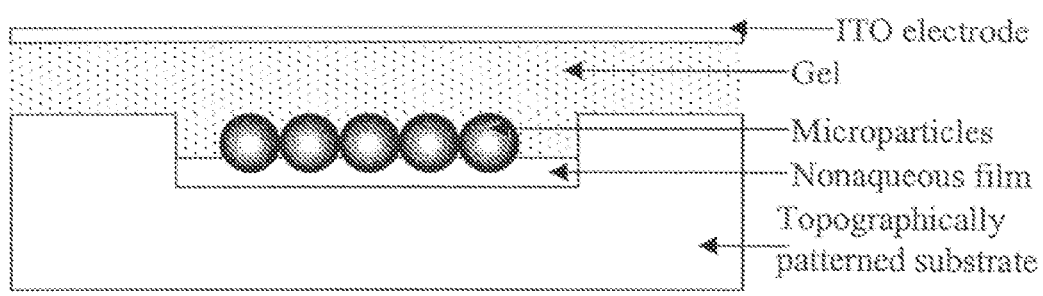
FIG. 4(b) is an illustration showing a flipped gel-particle composite film with the particles partially exposed.
Figure 4B:
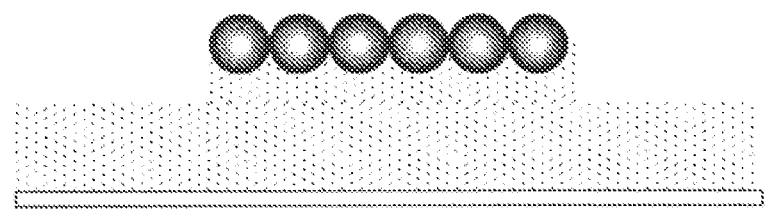

In certain other embodiments, the position of the bead array relative to the outer bounding surface of the embedding gel film may be controlled by assembling the microparticle array on a topographically patterned electrode surface exposing designated recesses of defined depth containing a non-aqueous phase that is non-miscible with an overlaid aqueous phase containing the microparticles as well as the chemical constituents required for gel film formation in accordance with the previous protocols (see FIG. 4(b)). Upon application of the requisite AC electric field, microparticles assemble within the designated recesses in such a way as to permit particles to remain partially submerged within the organic phase deposited into the recesses prior to assembly. Following assembly, gel formation is initiated in the manner described; however, the immiscibility of the two layered phases ensures that polymerization is confined to the aqueous phase, thereby leaving embedded microparticles partially exposed.

Figure 5:
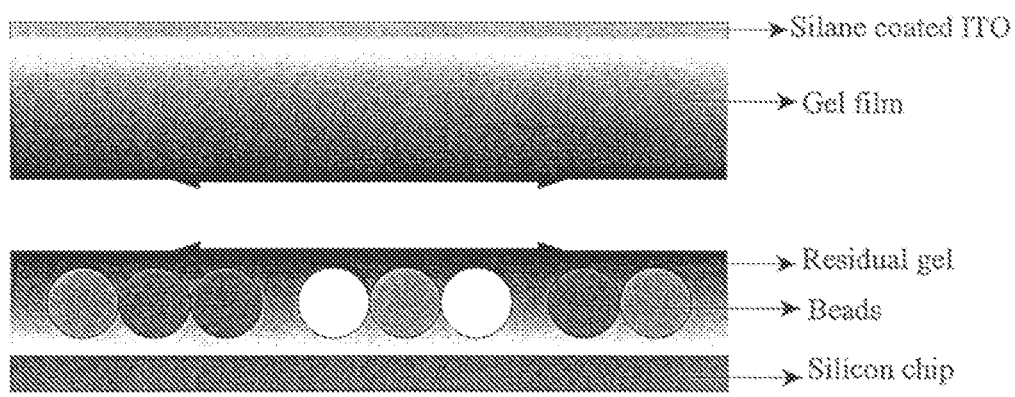
FIG. 5 is an illustration showing a cleaved gel-particle composite film.

In certain other embodiments, a cleaved gel is prepared, following the same principle as FlipGels. The basic differences are that a) the monomer concentrations used in the polymerization reaction are smaller (for example, ≤5% by weight) and b) the time of irradiation is shorter. Under these conditions, the degree of polymerization is not uniform throughout the thickness of the cell. Typically, the degree of polymerization and crosslinking is highest near the top electrode (e.g., ITO electrode) and progressively grows weaker as one approaches the bottom electrode (e.g., silicon chip). After gelation, on disassembling the LEAPS cell and pulling the two electrodes apart, such a gel typically fractures at a plane very close to the substrate surface (see FIG. 5). Thus, a layer of gel remains attached to the ITO-coated coverslide while the silicon retains the rest of the gel containing the assembled bead arrays. The silicon chip can now be used for a variety of assays with the assay solution location directly on top of the gel. In this case, the diffusion length of the molecules is reduced from that of a regular gel because the cleavage usually occurs just over the plane containing the bead array, leaving beads more accessible to molecules present in the solution above the gel.

Figure 6:
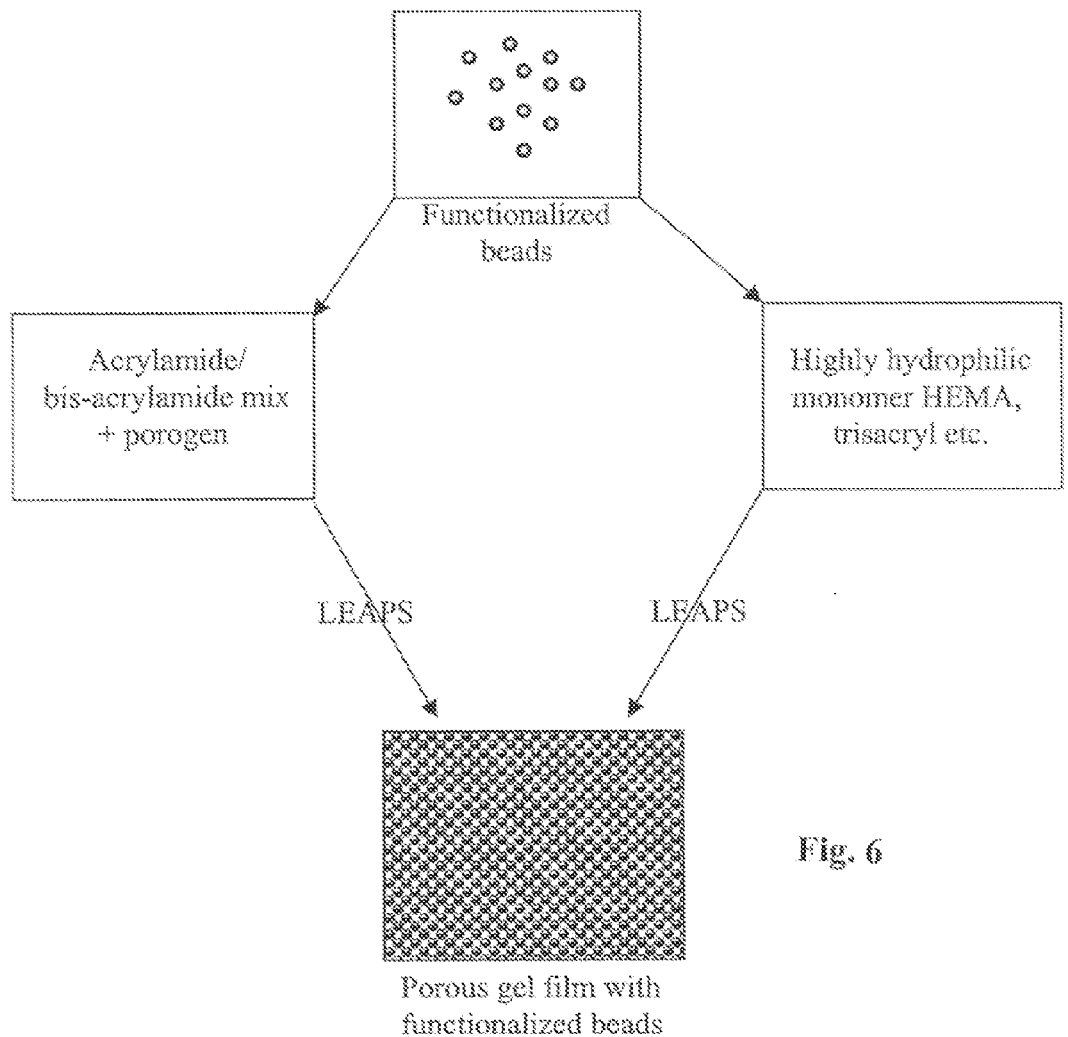
FIG. 6 is an illustration showing two exemplary processes for produce porous a gel-particle composite film.

Gels of the present invention may be porous. Polyacrylamide gels, for example, have typical pore sizes ranging from a few nm to 15-20 nm in highly diluted formulations. To facilitate the penetration of large DNA fragments and other molecules into gels, macroporous polyacrylamides may be prepared by polymerizing in the presence of pre-formed polymers such as poly(ethylene glycol)(PEG), polyvinyl pyrrolidone (PVP), hydroxymethyl cellulose (HMC) etc. (Righetti, P. G. and Gelfi, C. 1996. J. Chromatogr. B.699: 63-75.). Highly hydrophilic monomers, sush as tri-sacryl may also be used to produce highly porous gels (Gelfi, C., et al. 1992. J. Chromatogr. 608: 333-341). FIG. 6 illustrates the protocol to form a porous gel using preformed polymers.

Reversible Immobilization of Microparticles within Gel Films

Figure 7:
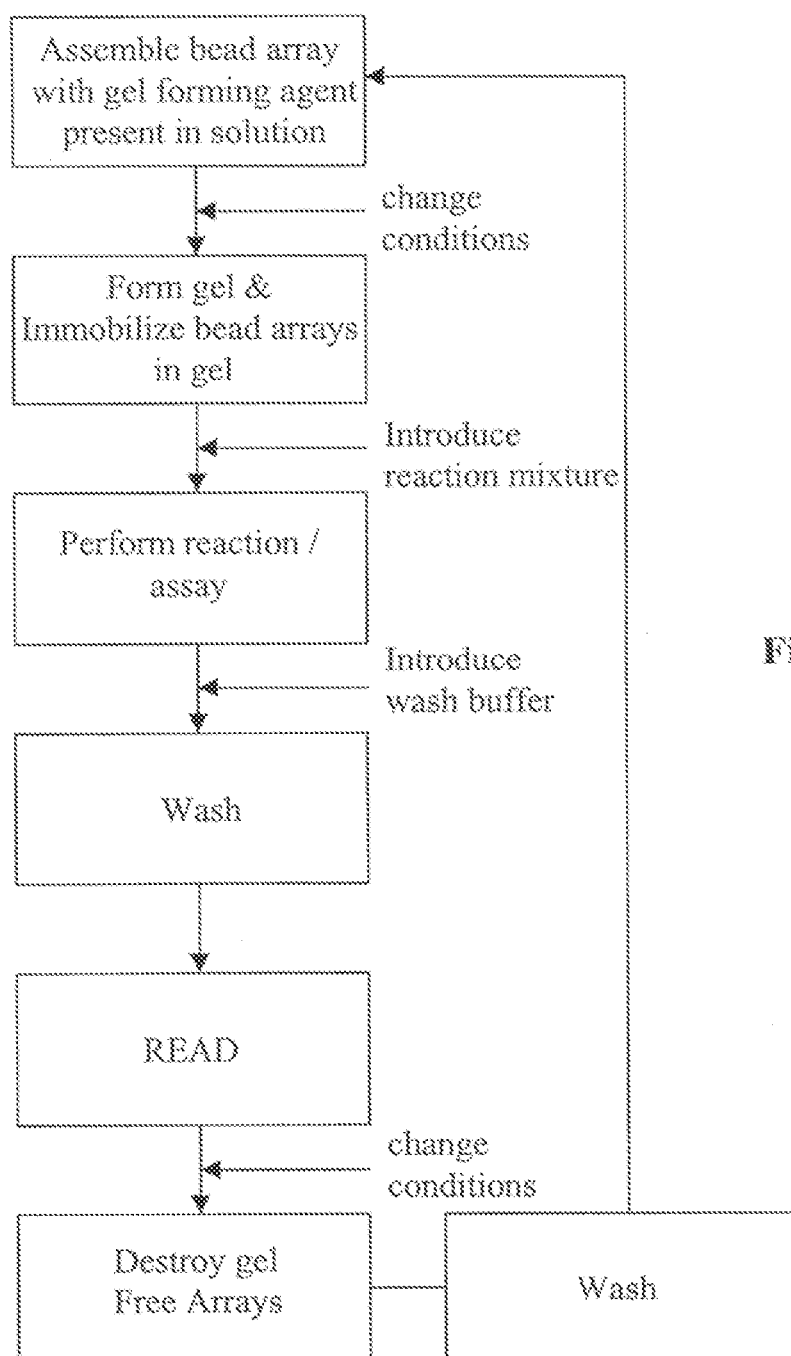
FIG. 7. is an illustration showing a process to produce a gel-particle composite film by reversible gelation.

So far, the process of forming polymeric films and polymer-film composites involved synthesis of chemically cross-linked polymers. The process of forming composite gel-particle films can, however, easily be extended to include physically gelling systems such as block copolymer gels, agarose gels, gelatin gels etc. Such gels consist of polymeric networks held together by physical rather than chemical crosslinking. The reversible gelation of such systems may, for example, be triggered thermally with the system existing as a sol at a high temperature and transforming into a gel on cooling and vice versa. The reversibility and the capability to form and immobilize bead arrays on cue allows to carry out a on-chip bioassay dynamically. An example of such a scheme is shown in FIG. 7.

EXAMPLES

The present invention will be better understood from the Experimental Details and Examples which follow. However, one skilled in the art will readily appreciate that the specific methods and results discussed are merely illustrative of the invention described in the claims which follow thereafter.

Example 1

AC Electric Field-Mediated Formation of Patterned Gel Films

LEAPS is carried out in a fluidic microcell formed by sandwiching a double-sided Kapton spacer of ~100 µm thickness (between a 1 cm×1 cm silicon chip (n-type, capped either by a uniform or a lithographically patterned thin $SiO_2$ layer), also serving as the bottom electrode, and a glass cover slip coated with indium tin oxide (ITO) to a typical sheet resistance of 1400 Ohm Square serving as the top electrode. FIG. 1 illustrates the various components of a LEAPS microcell.

The mixture of monomers and the initiator is introduced within the LEAPS cell and the electric field is applied. The thermal free radical polymerization is then initiated by heating the cell ~40-45° C. using an IR lamp (the polymerization can also be triggered by a step change in the bias voltage from a large positive value to a small positive value). Typical parameters of the AC electric field used for this particular example are $V_{p-p}$~5-8V and ω~1 kHz. This AC electric field-mediated protocol leads to the formation of a thin layer of hydrogel in predesignated areas (low impedance regions) on a $Si/SiO_x$ substrate.

Hydrogels are formed using azodiisobutyramidine dihydrochloride as a thermal initiator at a low concentration ensuring that the overall ionic strength of the polymerization mixture falls in the range of ~0.1 mM to 1.0 mM. The hydrogels are composed of a mixture of acrylamide and bisacrylamide of varying monomer concentrations from 20% to 5% (acrylamide:bisacrylamide=37.5:1, molar ratio).

Figure 2A:
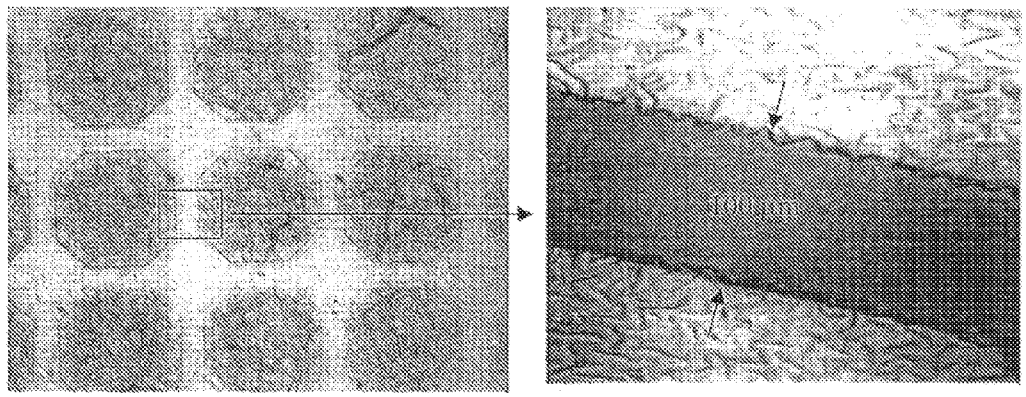
FIG. 2(a) contains a photograph showing a patterned gel film and a second photograph showing a close-up of a section of the film.
Figure 2B:
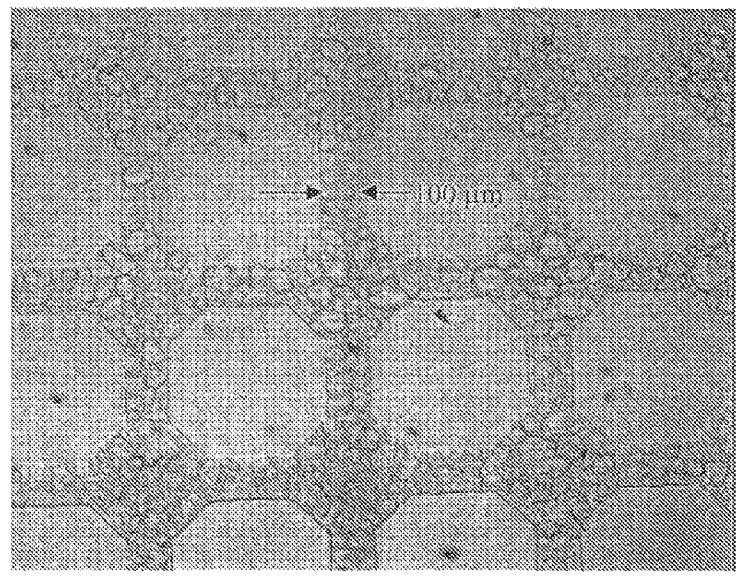
FIG. 2(b) is a photograph showing a free-standing gel film imaged in aqueous phase.

FIG. 2 illustrates a hydrogel formed on an interfacially patterned substrate under the action of electric field. The gel is formed exclusively in the low impedance regions (thin oxide) of the substrate. The wrinkled pattern seen on the hydrogel surface is caused by a mechanical instability set up in the gel during polymerization (Tanaka, T. 1987. Nature. 325:796; Warren, J. A. 1995. Spatio-Temporal Patterns, Ed. Cladis, P. E. and Palffy-Muhoroy, Addison-Wesley. 91-105).

Example 2

Preparation of Gel-Microparticle Hybrid Films

Figure 3A:
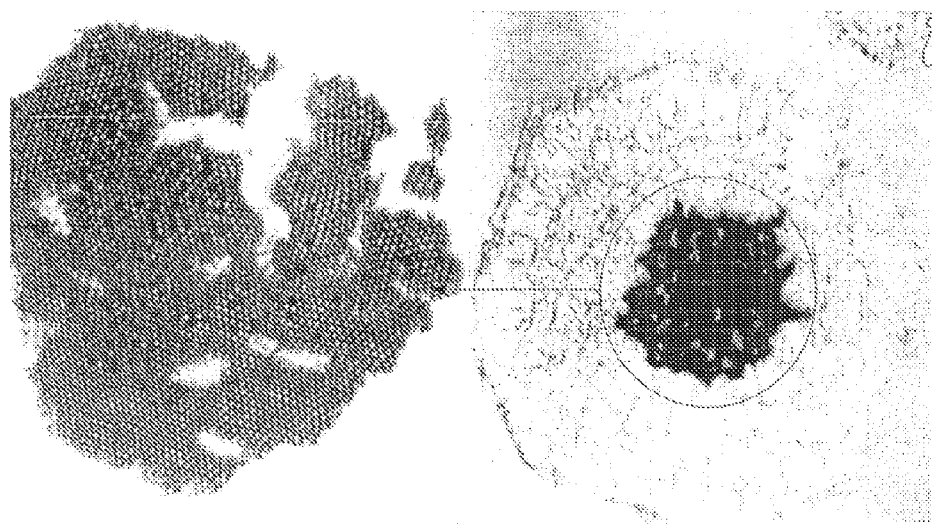
FIG. 3(a) contains a photograph showing a patterned gel-microparticle composite film created via thermal initiation and a close-up of the central section of the film.
Figure 3B:
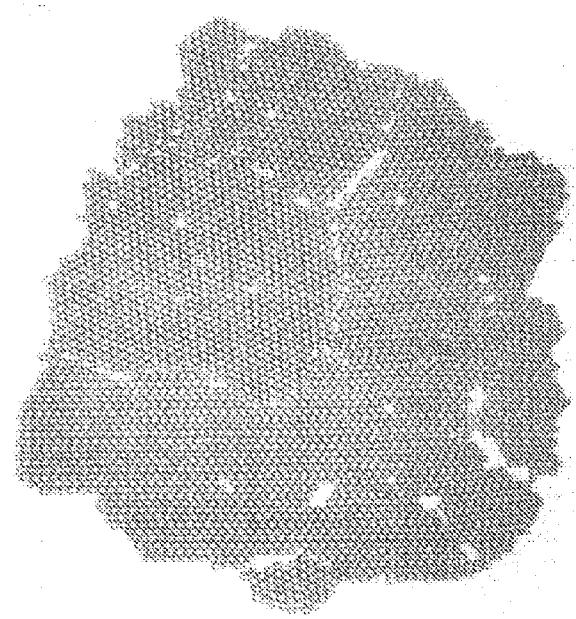
FIG. 3(b) is a photograph showing a monolithic gel-microparticle composite film created via UV-initiation.

Two stage process is used to synthesize polymer-microparticle film composites. First, ordered particle arrays are formed from a microparticle suspension also containing all ingredients required for subsequent in-situ gel formation in accordance with Example 1. LEAPS (see Example 1) is invoked to form arrays from particles suspended in a low viscosity monomer(s) dispersion mixed with an initiator in accordance with Example 1. Second, gels are formed, either via heat-initiated in-situ polymerization (Example 1) to form spatially patterned hybrid gels (see FIG. 3(a)) or via UV-initiated in-situ polymerization to form monolithic hybrid gels (see FIG. 3(b)), as described below.

To assemble particle arrays, AC voltages of 1-20 $V_{p-p}$ in a frequency range from 100's of hertz to several kilohertz are applied between the electrodes across the fluid gap. Fluid and particle transport and assembly are then monitored by video microscopy permitting frame capture and digitization of frames for further analysis.

Prior to assembly, particles stored in buffer are centrifuged and washed with deionized and ultrafiltered (conductivity<50 S cm$^{-1}$) distilled water three times. At the last wash, the monomer/crosslinker and initiator solution is added in amount so as to maintain the original concentration of particles. The initiator and/or the salt concentration is maintained at <=1 mM. The resulting particle suspension is applied to the LEAPS cell so as to fill the gap between the two electrodes. Anionic and cationic particles ranging from 0.5 μm to 15 μm in diameter, composed of silica, modified polystyrene or other polymers and functionalized with a variety of chemical surface groups, as well as functionalized core-shell particles obtained from a variety of manufacturers are used.

Following array assembly, and in the presence of the applied AC voltage, polymerization of the fluid phase is triggered, for example by using a mercury lamp source, to effectively entrap the particle array within the gel. A wide range of wavelengths spanning from about 250 nm to about 340 nm is suitable for the polymerization. FIG. 3 shows an example of a particle array immobilized in a polyacrylamide matrix. The concentration of the monomers was 10% and the the initiator used was a UV initiator Irgacure 2959® (2-Hydroxy-4'-hydroxyethoxy-2-methylpropiophenone, Ciba Geigy, Tarrytown, N.Y.). The initiator was added to the monomer to give a 1.5% by weight solution.

Example 3

Patterned Inorganic Materials

The ability to grow complex materials with small feature sizes is of much interest for the fabrication of structured and multifunctional films, biologically relevant heterostructures and photonic materials for optical and optoelectronic applications. Thus, processes to form patterns rapidly and directly to give geometrically as well as functionally organized structures without using complicated etching process or complicated chemical schemes can be extremely useful. In accordance with the present invention, the LEAPS-directed formation of patterned gel and gel-particle composite films provides for the fabrication of a variety of inorganic-organic, organic-organic, or fully inorganic composite structures.

Organic-organic composite—After formation of the patterned gel film on the low impedance areas of the substrate, the high impedance or the silicon oxide capped regions of the substrate can be decorated with a second polymer preferably through a process other than bulk radical polymerization (employed to synthesize the gel); for example covalent modification with silane polymers or oligomers, polyelectrolyte adsorption, hydrophobic interaction, hydrogen bonding etc. Following such a process the earlier gel layer can be lifted off, enabling the formation of complementary patterned polymer or gel film.

Figure 8:
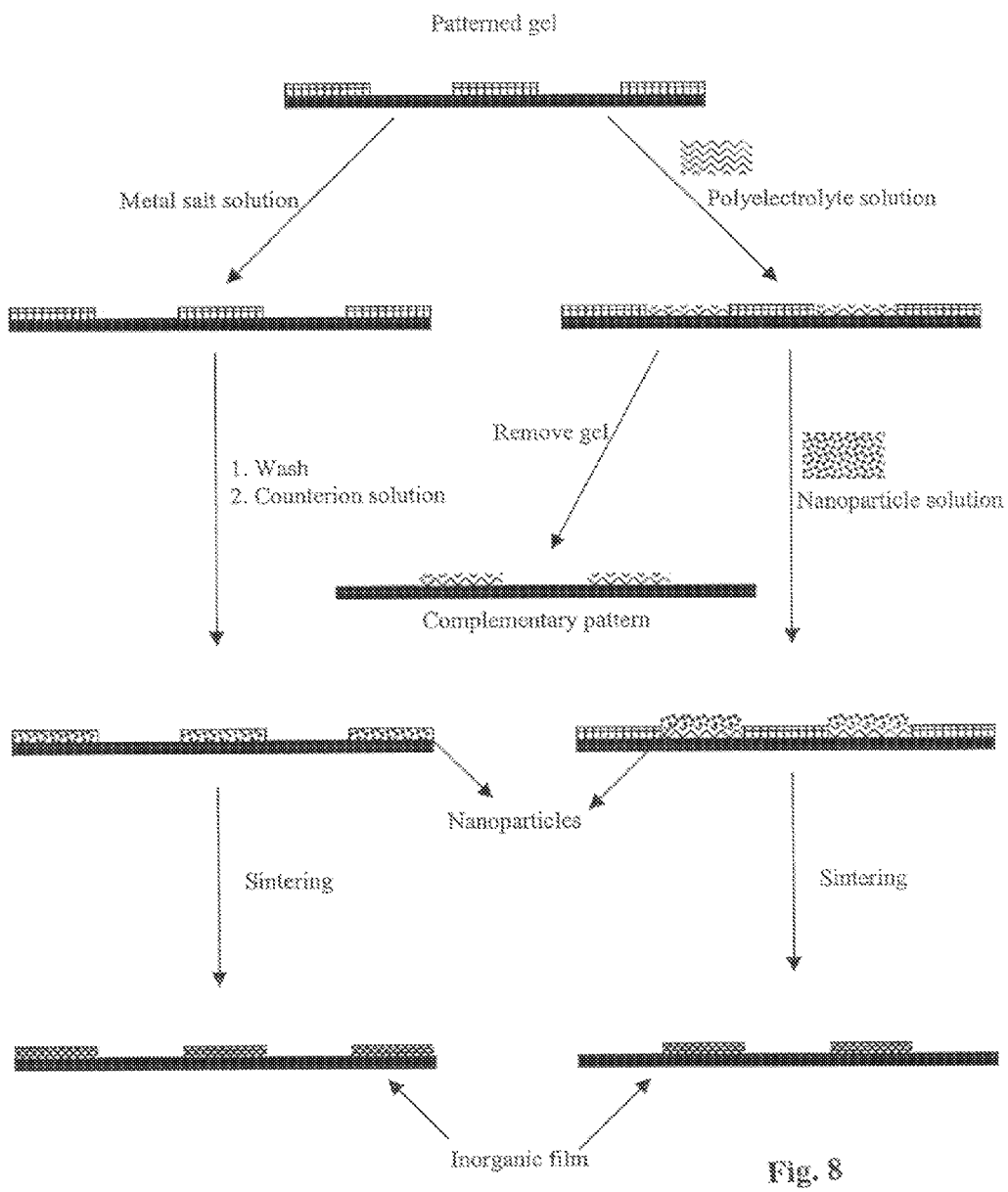
FIG. 8. is an illustration showing a process to produce inorganic-organic hybrid films.

Organic-inorganic composite—FIG. 8 outlines the scheme of the basic procedure for making metal (Au, Ag, Cu etc.), metal oxide ($Fe_2O_3$, $Co_3O_4$, NiO) or semiconductor (CdS, PbS, ZnS) nanoparticles in the patterned gel matrix. The process involves exposing the patterned gel on a substrate to a solution of a metal salt, followed by DI water rinse and exposure to reducing agent (in case of the metal) or second salt solution in other cases. The nucleation and growth of the nanoparticles take place within the hydrophilic domains defined by the gel film.

Inorganic composite—Fully inorganic structures can easily be generated from the structures generated above by calcining at high temperatures so as to burn off the organic component.

Example 4

Interconnections

The realization of interconnections in the form of electrical, optical or chemical conduits in small devices represents a critical aspect of the realization of integrated electronic, optoelectronic or biochemical processors. The methods of the present invention permit the assembly of linear microparticle assemblies in accordance with LEAPS, either under illumination or on patterned EIS interfaces, and their subsequent immobilization, for example by embedding within a gel matrix as described herein.

Electrical Conduit—Following completion of the assembly of metal core/polymer shell particles into linear configurations, rapid heating of the silicon substrate, for example by exposure to pulsed laser light, will melt away the polymer components and fuse adjacent metal cores. Of interest in this application will be particles containing solid metal (Cu, Ni) cores or particles containing metal nanoclusters dispersed into a polymer matrix which may be prepared by methods known to the art.

Optical Conduit—Within a linear assembly of glass particles, illuminated with focused light, particles will guide scattered or emitted light to their respective nearest neighbors. Thus, individual beads may be illuminated by focused laser light and can serve as secondary sources to illuminate adjacent particles within the linear assembly.

Chemical Conduit—Following completion of the assembly of polymer particles into linear, circular or other desired configurations, particles are permanently immobilized on the substrate, for example by non-specific adsorption, this structure serves as a positive mold around which a gel matrix is grown which is the lifted to reveal complementary negative surface relief, such structures can be closed by fusion with a substrate or another gel and can serve as linear conduits for the transport of biomolecules or other materials.

Example 5

Self-Supporting Magnetic Gel Films

Free standing gel microparticle hybrid films similar to those described in the detailed description section are prepared using functionalized and superparamagnetic microparticles or a mixture of superparamagnetic particles with (non-magnetic) color-encoded and functionalized microparticles. Incorporation of magnetically responsive particles permits the separation of the gel film from a solution containing biological sample by application of a magnetic field.

This is of particular benefit in carrying out multi-step biological assay protocols.

Figure 9:
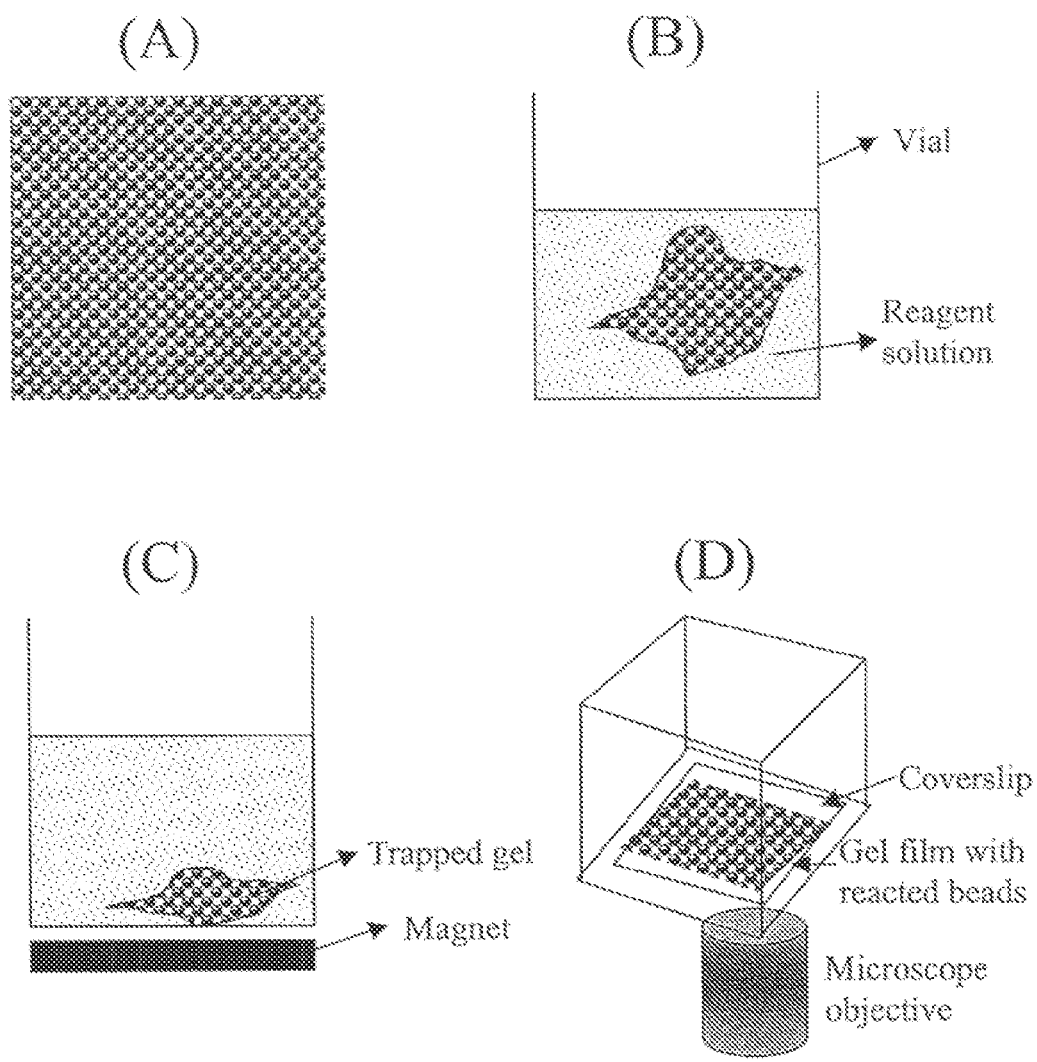
FIG. 9. is an illustration showing a process to produce and characterize a magnetic gel-particle composite film.

In a protocol enabled by the self supporting magnetic gel films of the instant invention (FIG. 9A), an in-tube binding assay probing analyte molecules present in solution by permitting capture to bead-displayed receptors is performed under conditions permitting the magnetic gel-microparticle film to remain in suspension (FIG. 9B). Following completion of the assay, magnetic separation (FIG. 9C), achieved by application of a magnetic field, permits the temporary immobilization of the gel film on a transparent surface of the reaction chamber. Following fluid and/or buffer exchange, all excess fluid is removed in the last step, leaving the hydrated gel film exfoliated on the transparent surface even in the absence of the magnetic field (FIG. 9D). Images recording the results of the binding assay may now be obtained using a microscope. In a preferred embodiment, a coverslip is positioned above the film to prevent evaporation which may lead to buckling of the film.

A combination of magnetic oligo(dt) and antibody functionalized gel matrix may also be used to carry out simultaneous capture of target cells to gel via cell-surface antigens, followed by lysing of the cell and capture of genomic DNA to magnetic and oligonucleotide functionalized microparticles within the gel.

Example 6

Hybridization Assay in Gel-Microparticle Hybrid Films

DNA hybridization assays is conducted using Oligo probe (short single stranded DNA fragments) functionalized particles embedded in gels. The probe coated particles are made as follows. Neutravidin coated beads are washed thoroughly in salinated PBS of pH 7.4. The biotinylated probes are then added to the bead suspension and mixture incubated at room temperature for 90 min. The probe-coated beads are then stored in PBS solution containing 0.01% Triton.

The targets for DNA hybridization reactions can be either single-stranded or double-stranded molecules. Single-stranded DNA of a given length and sequence were synthesized chemically (Integrated DNA Technologies, Coralville, Iowa). Double stranded DNA is a PCR-amplified product directly obtained from genomic DNA of patient samples. The PCR product is produced using fluorescence-labeled primers. After preparation, the primers are removed by a PCR purification kit (Qiagen) and the resultant solution can be used in the assay. Single stranded DNA can also be prepared from double stranded sample by digesting the antisense strand. For this purpose the antisense primers used in PCR amplification have to designed with a phosphate group at the 5' end. A strandase enzyme is then used to digest the antisense primer. In either case, the DNA at the end of the process in suspended in Tris-EDTA buffer and the concentration is determined using UV optical density measurements.

Before hybridization, the double stranded DNA has to be denatured to yield single strands. For this, the DNA is diluted with Tris EDTA buffer and heated in a sand bath at 95 C for 1 min. It is stored in ice before use. It is then mixed with an equal volume of tetramethylammonium chloride to yield a desired concentration of DNA for the reaction.

Two types of beads, internally stained with different fluorescent dyes and each bearing a different probe, are used for the reaction. One of the probes used is a perfect match with the target strand while the other sequence represents a deletion of 3 bases.

The beads are washed three times with distilled water and finally suspended in 5% monomer solution and initiator concentration as described earlier. The beads are assembled into arrays in a LEAPS cell using 4 V peak to peak AC voltage and frequency 500 Hz. After assembly, the cell is irradiated with UV light for ~3 min. This will yield a Flip Gel which is then used for hybridization. The Flip Gel is attached gel-side up to a polished silicon wafer using single-sided tape. 1 ul of target containing 100 ng/ul dna was diluted using 24 ul of TE and 25 ul of 2× TMAC. From the resultant solution 10 ul was added to the gel for reaction. The wafer was enclosed in an air-tight wafer holding container, sealed and set on a shaker at 50 rpm in an oven at 55 C. The reaction was conducted for 30 min. At the end of the procedure, the gel was washed twice in 1× TMAC equilibrated at 55 C.

Figure 10:
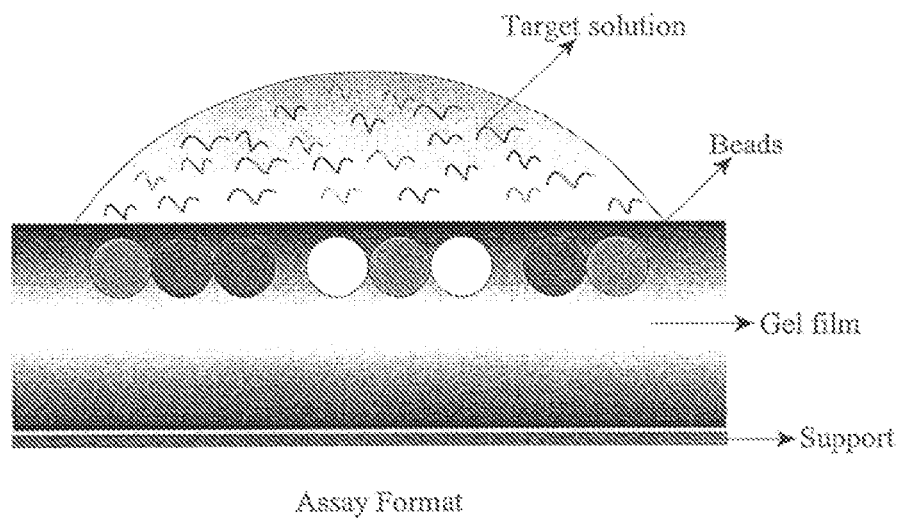
FIG. 10. is an illustration showing a DNA hybridization assay using a flipped polymer-gel composite film.
Figure 10:
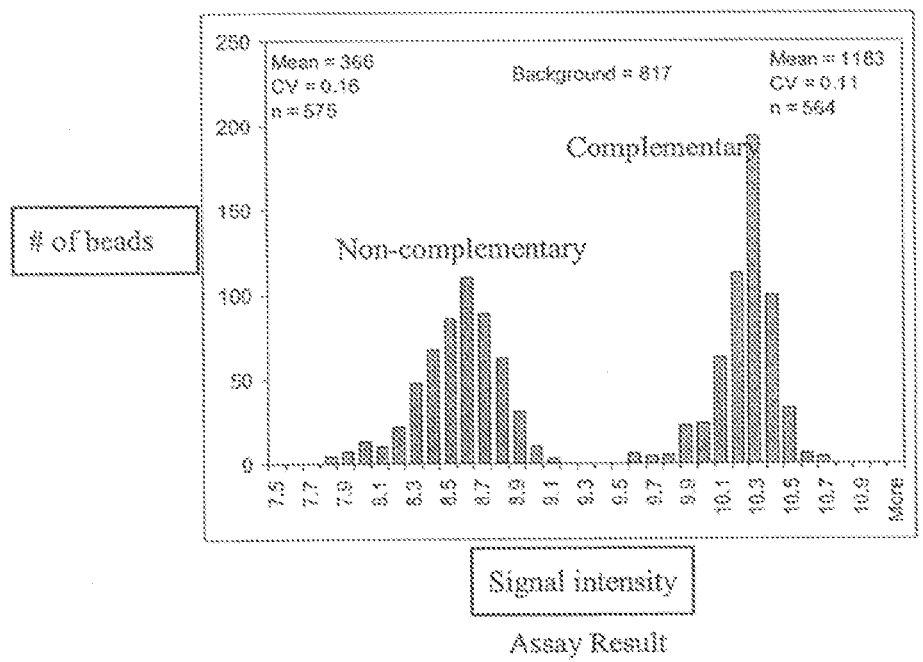

The gels are prepared for imaging by applying a coverslip on them. Images are taken in the bright field and the Cy5 channels (probes labeled with Cy5). To distinguish the two different types of particles in the arrays, images are also taken at two other color channels appropriate for the internal encoding dyes. The set of four images are then analyzed to yield the assay results (see FIG. 10)

Example 7

DNA Electrophoresis and Hybridization in Gel-Microparticle Hybrid Films

Figure 11:
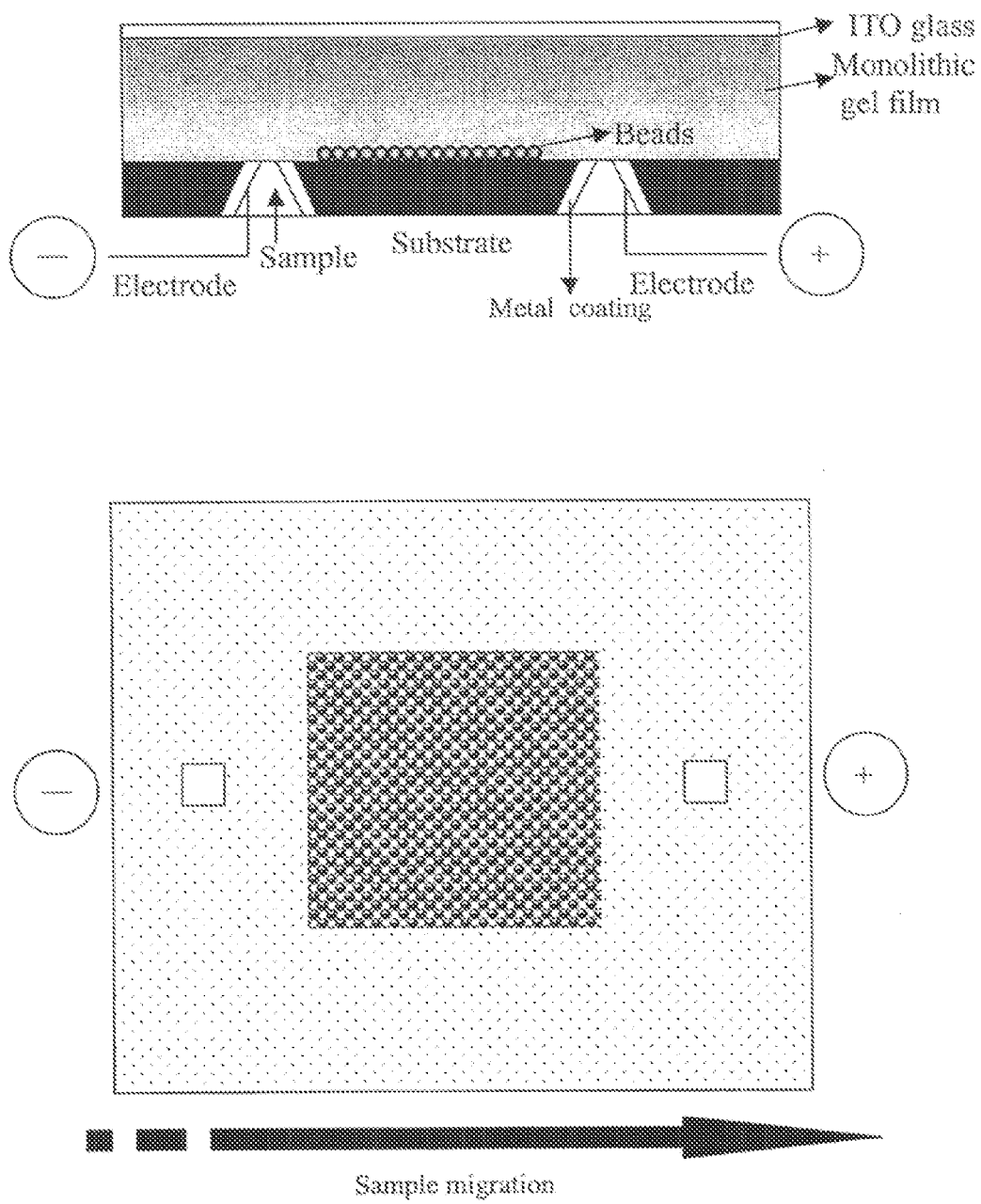
FIG. 11. is an illustration showing electrophoretically assisted DNA hybridization.

One method of performing rapid nucleic acid hybridization assays in the gel-microparticle hybrid films involves the use of D.C. electric fields to induce electrophoresis of target nucleic acid strands. This is especially relevant in case of large target fragments whose diffusion inside the gels are expected to be low. Typically the samples for analysis are denatured and electrophoresed through the gel-microparticle hybrid films, as the complementary single-stranded nucleic acid targets contact the capture probe (oligo) functionalized beads, they hybridize and are quantitatively immobilized on the microparticle surface. The non-complementary strands does not hybridize with the capture probe and migrate through the gel unimpeded. The hybridization is detected using luminescent labels associated with the sample nucleic acid. FIG. 11 two different possible geometries for carrying out electrophoretically assisted hybridization in gel-microparticle hybrid films.

Example 8

Immunoassay in Gel-Microparticle Hybrid Films

Protein assays are readily performed on supported gel s, self-supporting gels, Flip Gels and Cleaved Gels. An example of immunoassays performed is the binding reaction between Mouse IgG and Goat Anti-Mouse IgG. For this reaction, the beads used in the reaction are surface-coated with the Mouse IgG. For this purpose, neutravidin-coated particles of size 3.2 µm are incubated overnight with the Mouse antibody (SigmaChem) in a phosphate buffer solution of pH 7.2. After the coating process, the particles are washed thoroughly with PBS containing bovine serum albumin.

The target molecules of goat anti-mouse IgG are labeled with a monofunctional fluorescent dye Cy5.5 (Amersham). The NHS-ester-containing dye attaches to the amine groups of the IgG by following a manufacturer supplied protocol. The dye and the IgG molecules are incubated for 1 hr at pH 9.3. The free dye is then separated from the labeled molecules using a gel filtration column and phosphate-buffered saline as the separation buffer. The concentration of IgG in the sample and the number of dye molecules per molecule of IgG is calculated.

Two types of particles are used for the reaction, one for the assay and the other as a negative control. They are distinguished by the use of internal encoding dyes which have excitation and emission at different wavelength from those of Cy5.5. One of the types of particles is coated with Mouse IgG as described above and the other has merely a coating of neutravidin. A mixture of these two types is spun down and washed with D.I. water containing 0.01% Triton three times. After the last spin, the particles are suspended in the monomer mixture containing 10% monomer solution and the UV-initiator in amounts described earlier. The particles are assembled in a LEAPS cell and irradiated to form a monolithic gel. Depending of the concentration and the time of irradiation, a regular, Flip Gel or Cleaved Gel is formed.

Figure 12:
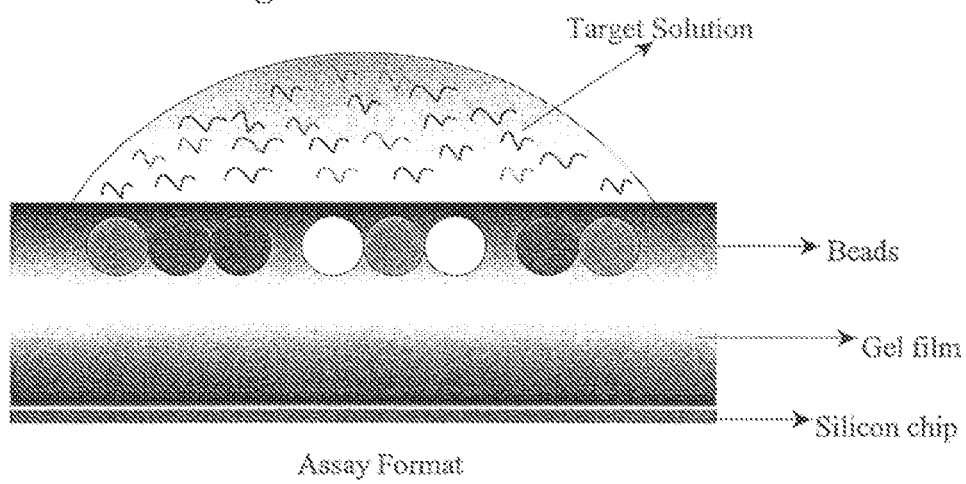
FIG. 12. is an illustration showing an immunoassay using a flipped polymer-gel composite film.
Figure 12:
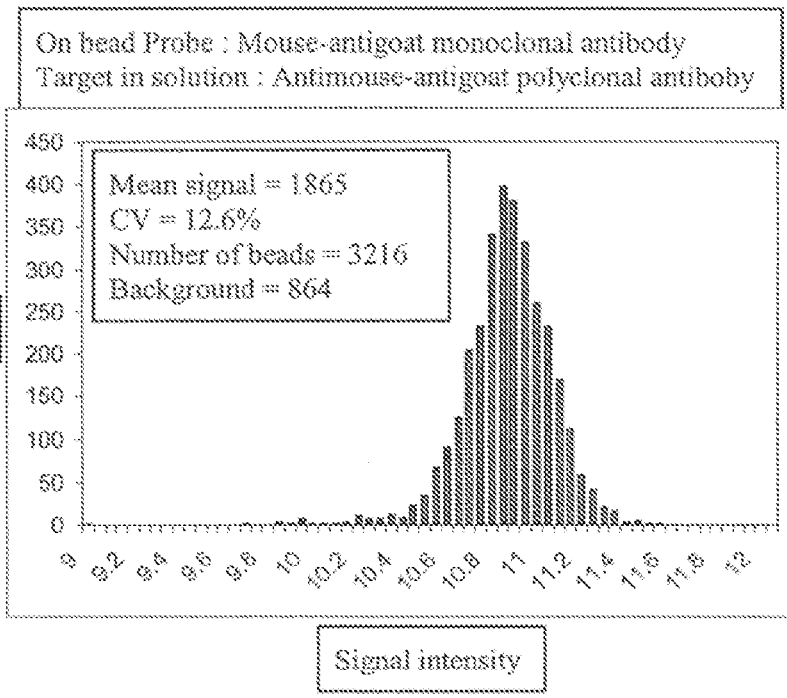

The gel is placed with the support (coverslide in case of Flip Gel, silicon chip in case of regular and Cleaved Gels) gel side up. A given volume (10 µl) of a known concentration of the Goat anti-Mouse IgG placed on the gel. The gel with the solution is then enclosed in an airtight container and put on a shaker operating at 50 rpm in an oven at 37 C for one hour. After binding has occurred, the gel os loaded with 20 µl of alkaline SDS (Tris base containing 10% SDS) for 30 min to reduce nonspecific binding. The gel is then washed with alkaline SDS twice and prepared for imaging. A coverslip is placed on the wet gel and images are taken in the bright field, and the Cy5.5 channel. To distinguish the two different types of particles in the arrays, images are also taken at two other color channels appropriate for the internal encoding dyes. The images are then analyzed to establish the mean binding intensity and the intensity distribution of each type of bead in the mixture (see FIG. 12).

Example 9

Bioanalytical Assay with Integrated Filtering and Specific Capture

The gel-microparticle hybrid film is ideal for selectively capturing specific nucleic acids or proteins from a crude mixture like whole blood or cell lysate. Typically a crude sample containing whole blood is contacted with the gel containing microparticles functionalized with capture probe molecules of interest. The red and white cells are automatically screened by the gel on the basis of their size. The complementary components from plasma bind to the capture probe coated beads. Non-complementary components can then be easily washed off.

Example 10

Recording of Assay Images from Hybrid Films

In accordance with the methods of the present invention, a Nikon Eclipse E-600FN epifluorescence microscope equipped with 150 W xenon-arc lamp and a Nikon 20×0.75 NA air objective fitted with an optimized set of filter cubes for the selection of fluorophores was used for all measurements. Images were recorded with a cooled 16 bit CCD camera (Apogee Instruments Inc.). The exposure/integration times for the various preparations varied between 25 ms to 500 ms. User interfaced programs for analysis of images and assay results were developed using MATLAB which was run on PC. Image collection and analysis may then be performed.

Example 11

Multiple Samples per Chip

Figure 13:
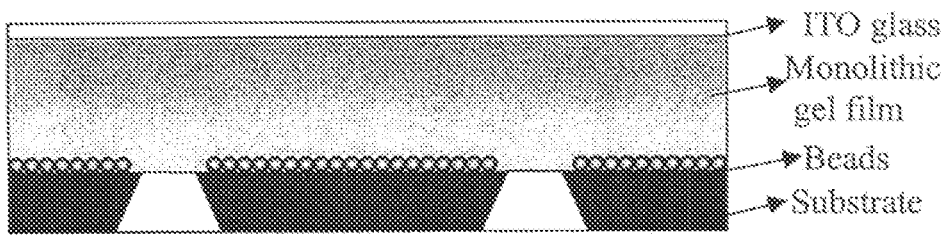
FIG. 13. is an illustration showing the analysis of multiple samples on a monolithic gel chip.
Figure 13:
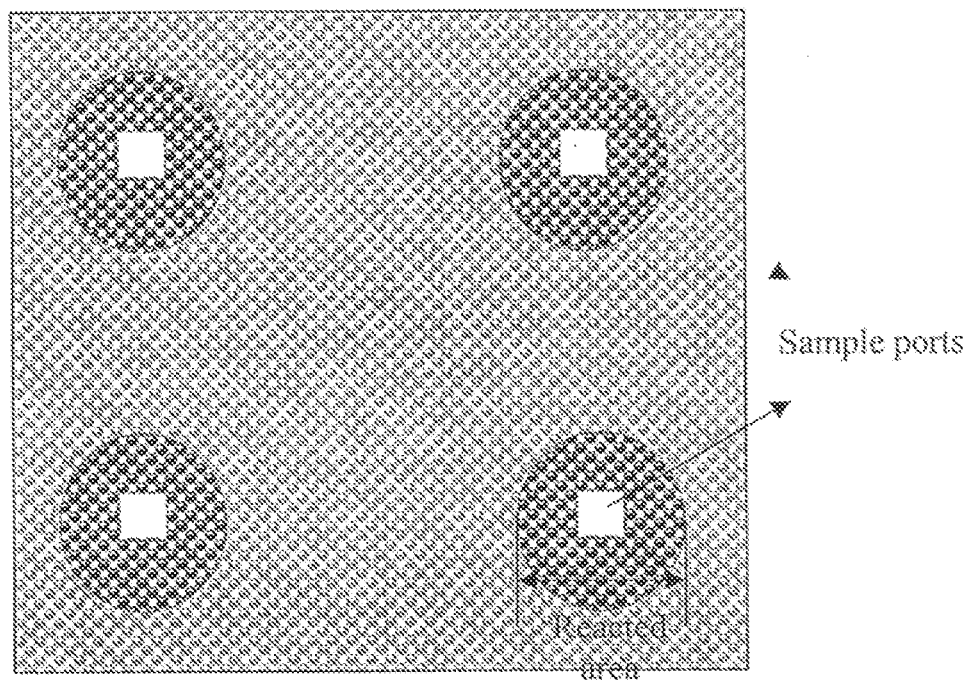
Figure 14:
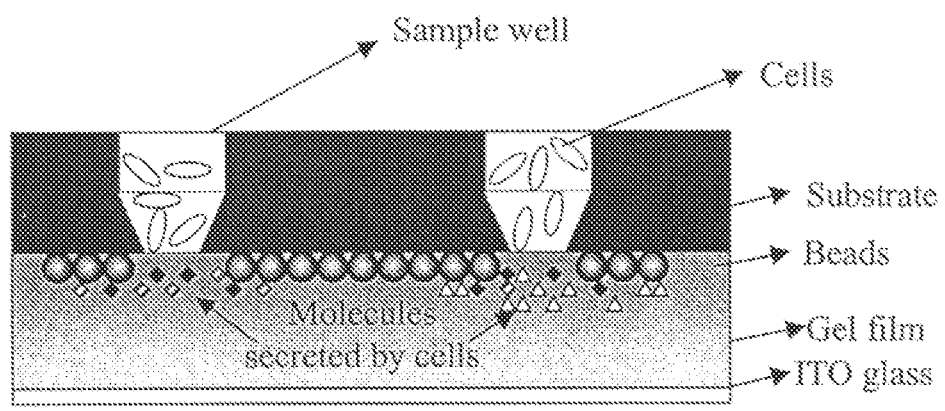
FIG. 14. is an illustration showing a process to implement a cell-bead heteroreactor.

FIG. 13 illustrates a method of carrying out multiplexed assays for multiple samples using the same monolithic gel film containing multiple bead arrays. A gel film containing bead arrays is synthesized (as described in Example 3) on an interfacially patterned silicon chip into which through holes have been made at four corners (choice of this geometry is arbitrary and is chosen here for illustrative purposes only, in principle a wide variety of designs and number of holes can be chosen). The samples are added by pipetting through the back of the chip, and the sample is allowed to spread diffusively and react with the surrounding particles as shown in FIG. 13. Depending on the length of the incubation time the area of the reacted patch will vary (Area~tD, where t reaction time and D diffusion coefficient of the target in gel).

Example 12

Cell-Based Heteroreactor

A cell-bead heteroreactor is constructed on a silicon substrate containing etched through-holes serving as fluidic interconnects. First, a gel-microparticle composite film is formed in accordance with Example 3 in the fluidic compartment defined by (the front side of) the silicon electrode and the ITO-coated glass electrode. Next, suspensions of cells are introduced into the tapered etched through-holes on the backside of the silicon electrode. Molecules secreted from cells within these microwell structures are now allowed to diffuse into the gel where they are detected by capture to functionalized beads within the previously assembled array. Alternatively, cells within the microwells may be lysed, and released genomic DNA may be enzymatically fragmented to allow sufficiently small fragments to diffuse into the gel where they are captured by hybridization to functionalized beads within the previously formed array while large constituents of the lysate are kept out. This second structure can remain open, and may be fashioned to exhibit the dimensions and form factors, for example of a 1536-well microplates; alternatively, a second fluidic compartment may be formed by (the back side of) the silicon electrode and a third delimiting planar substrate to permit microfluidic transport of cell suspensions.

Example 13

Co-assembly of Heteroparticle Arrays

Figure 15:
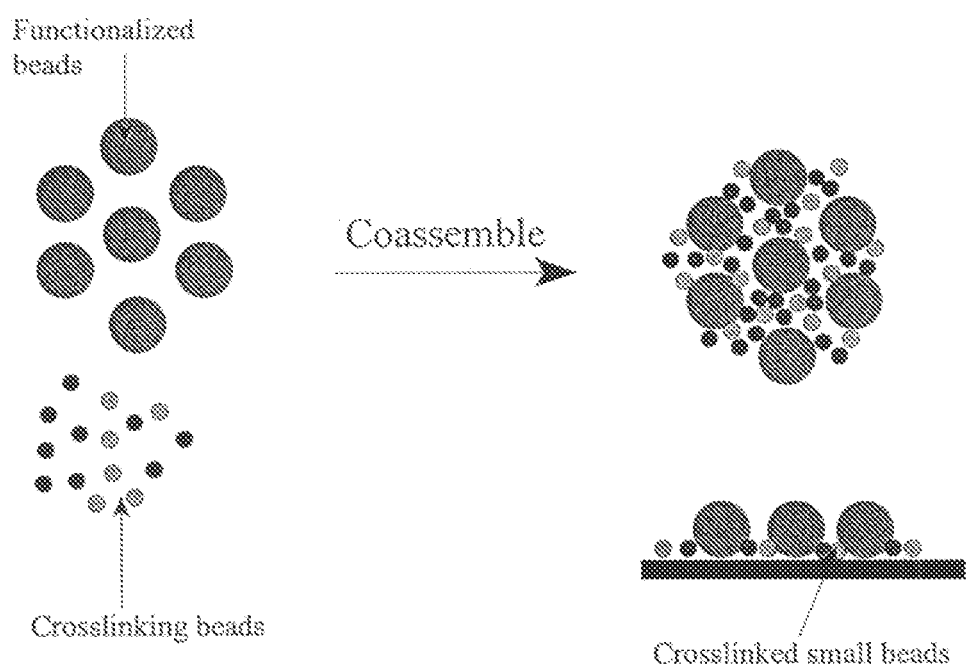
FIG. 15. is an illustration showing a heteroparticle arrays.

LEAPS enables the co-assembly of a binary mixture of smaller beads along with larger assay beads in designated areas of the substrate (FIG. 15). Once arranged in an array format the smaller beads then undergo two-dimensional crosslinking since they contain either complementary charge or reactive groups. The two-dimensional crosslinked aggregate created in the process acts as an inert mold for the larger assay beads which are thus immobilized. The advantages of the protocol include the ease of implementation, control of spatial localization and good immobilization efficiency.

Example 14

Fabrication of an Enzyme Sensor by Directed Self-Assembly

In accordance with the methods of the present invention, the combination of LEAPS-mediated active assembly of an array of functionalized microparticles and the chemical synthesis of a polymeric gel film permits the in-situ synthesis of a variety of sensors.

Figure 16:
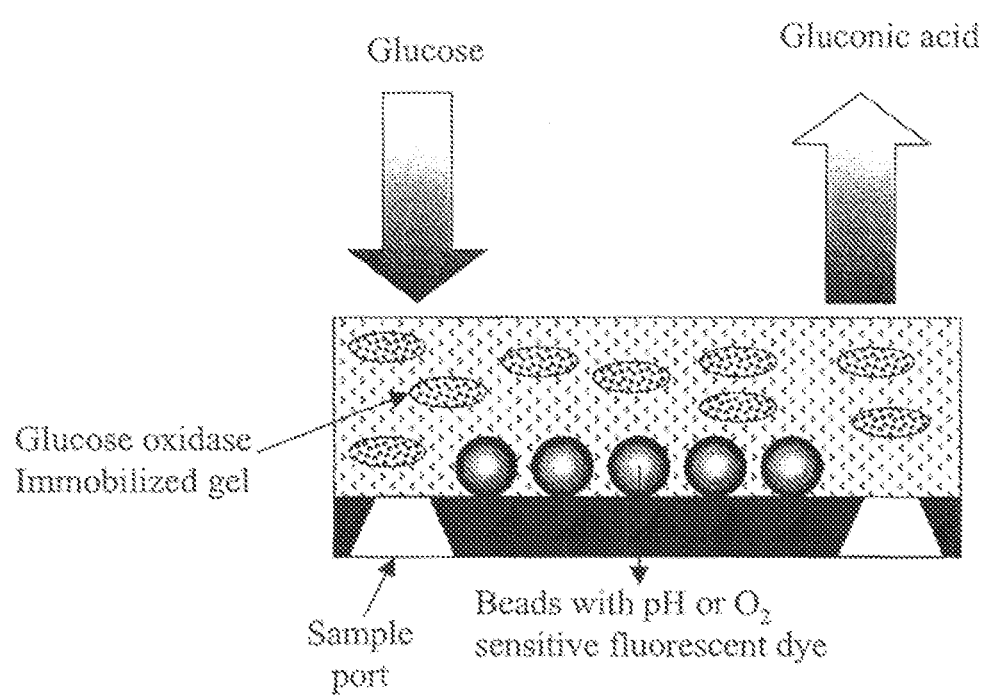
FIG. 16. is an illustration showing a glucose biosensor.

Thus, given a fluidic microreactors composed of patterned silicon/silicon oxide chip and ITO-coated glass electrodes arranged in sandwich geometry as illustrated in FIG. 1, a glucose sensor based on a gel-microparticle composite film is constructed by the following sequence of steps where, in a preferred embodiment, the silicon electrode contains a set of access ports illustrated previously in FIGS. 13. The resulting sensor (shown in FIG. 16) utilizes the enzyme glucose-oxidase immobilized covalently in the gel film, with microparticles functionalized or loaded with pH-sensitive or oxygen-sensitive fluorescent dyes.

1-inject solution containing
   functionalized particles
      displaying pH-sensitive or oxygen-sensitive dyes known to the art
   reaction mixture containing precursors and ingredients for gel formation
   functionalized glucose oxidase
2-apply AC electric field to trigger LEAPS and produce microparticle array(s)
3-trigger gel formation by UV-initiation of polymerization
   to form patterned or monolithic gel film incorporating functionalized glucose oxidase
4-remove electric field and UV illumination
5-inject (glucose-containing) sample into space below patterned silicon chip to initiate GOx
diffusion of sample into gel matrix; in the presence of glucose, the following reaction occurs

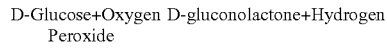

D-Glucose+Oxygen D-gluconolactone+Hydrogen Peroxide 6-monitor reaction shown below by recording fluorescence intensity from microparticle array; reduced oxygen levels or the reduced pH in the local gel environment, and their effect on the bead-anchored dyes, serve as an indirect indication of glucose concentration.

Example 15

Fabrication of a Gel-Embedded Planar Array of Vesicles

There is a growing interest in developing miniaturized sensing, sampling and signal amplifying structures coupled with an analytical measuring element to carry out a variety of bioassays. The sensing component typically reacts or interacts with an analyte of interest to produce a response that can be quantified by an electrical or optical transducer. The most common configurations use immobilized biomolecules on solid phase supports while another less common approach uses living microorganisms or cells or tissues as the sensing structure.

Unilamellar vesicles are composed of a single lipid bilayer shell that encloses an entrapped aqueous compartment; methods have been described to prepare giant unilamellar vesicles whose size approaches that of cells. Such vesicles are attractive as ultra-small reaction vessels or "artificial organelles" in which the reaction is confined and separated from the external medium. Vesicles containing reconstituted integral membrane proteins provide a synthetic chemical structure to study the function of such proteins including many cell surface receptors. In addition, the surface of such vesicles can be decorated with a variety of receptor moieties mimicking a natural cell and allowing complex biochemical reactions and/or interactions to be studied (Lasic, D. D. Ed. "Liposomes : From Physics to Applications", 1$^{st}$ ed., Elsevier Science B. V.: Amsterdam, 1993.)

Given a mixture of vesicles of two types, each containing one of the reactants of a reaction of type A+B-->C, two of vesicles of different type may be brought into close proximity, fore example, by forming a close-packed planar array, and may then be fused using a pulsed electric field in accordance with methods known to the art, in order to form a larger vesicle in which the reaction A+B->C is now performed. In a preferred embodiment, A may represent an enzyme, B a substrate, C the product of the enzymecatalyzed reaction. This reaction scheme may be generalized to involve more than two reactants.

Vesicles entrapping a single functionalized and encoded microparticle can be prepared by methods known to the art. Using methods of the present invention, microparticle encoded, gel-embedded vesicle arrays may be prepared (see Examples 1, 2, 3 and 4) to provide for a synthetic assay format in which the function of multiple cell-surface receptors such as ion channels may be quantitatively characterized.

Figure 17:
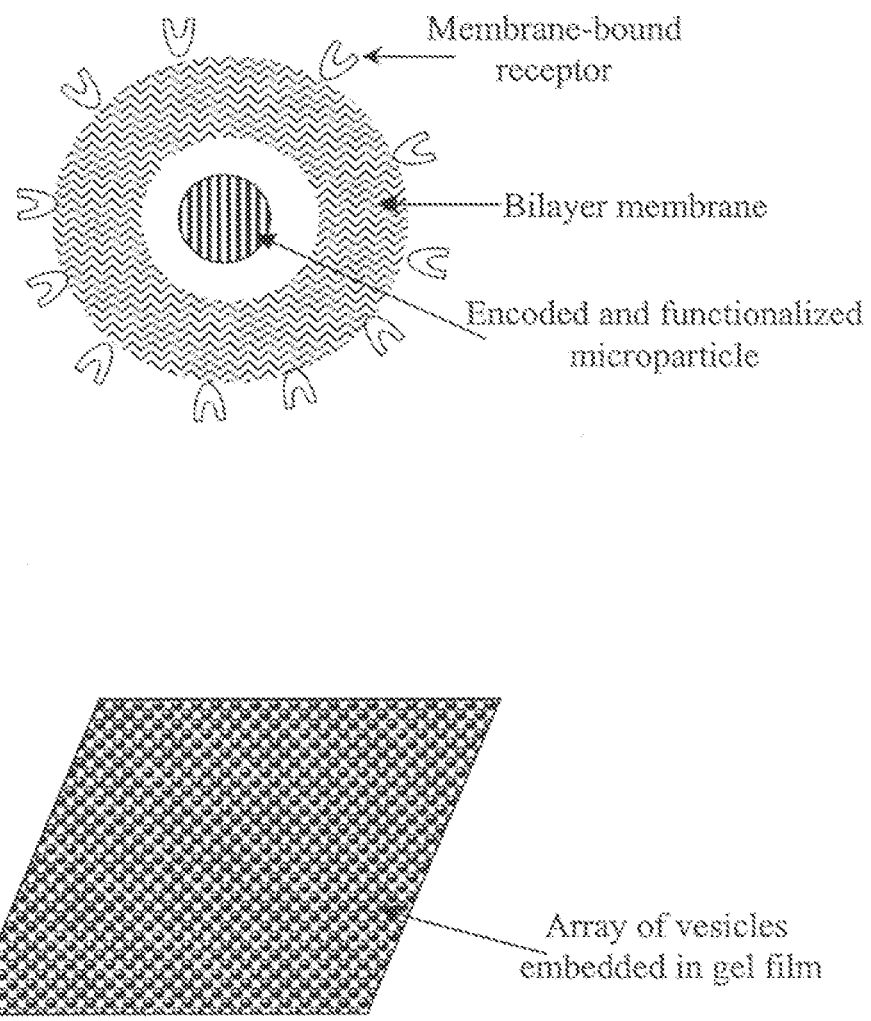
FIG. 17. is an illustration showing microparticle-encoded vesicles embedded in a gel film.

A variety of complex biochemical assays may be performed using such a composite structure. As illustrated in FIG. 17, an array of vesicles displaying multiple types of receptors, each vesicle displaying only one type of receptor and containing a corresponding fluorescently stained and functionalized microparticle, is immobilized in a thin gel film using methods disclosed herein; the fluorescent color of the particle is used to determine the identity of the receptor on the vesicle. In addition, the microparticle, is also functionalized on its surface with a measuring element such as an environmentally sensitive fluorescent dye to indicate a change in the internal aqueous compartment of the vesicle following a binding event on its surface.

Example 16

Gel-Embedded Cellular Arrays and Their Use in Cell-Based Functional Assays

The entrapment and immobilization of viable cells in various polymeric matrices, natural or synthetic, including polyacrylamide (Vorlop, K. et al. Biotechnol. Tech. 6:483 (1992)) have been reported, primarily in connection with biocatalysis (Willaert, P. G. et al. (Eds.), "Immobilized living cell systems: Modeling and experimental methods." Wiley, New York, 1996). Polymeric matrices can provide a hydrated environment containing nutrients and cofactors needed for cellular activity and growth. To minimize mass transfer limitations, methods of the present invention may be used to immobilize arrays of cells in a thin and porous gel film.

In accordance with the methods of the present invention, the process of forming a composite structure containing cell arrays entrapped in a patterned or monolithic gel film consists of two stages. First, ordered cell arrays are formed from a cell suspension also containing all ingredients required for subsequent in-situ gel formation in accordance with Example 1. In a preferred embodiment of the array assembly process, LEAPS (see Example 1) is invoked to form arrays from cells suspended in a low viscosity monomer(s) dispersion mixed with an initiator in accordance with Example 1. Second, gels films are formed, either via heat-initiated in-situ polymerization to form a spatially patterned composite or via UV-initiated in-situ polymerization to form a monolithic composite, as described (see Example 2).

The immobilized cell array system of the instant invention is useful for a variety of assay formats. For example, to analyze and quantify several molecular targets within a sample substance, the methods of the present invention provides for the means to form a gel-embedded cell array displaying a plurality of receptors (to one or more of the targets) which may be exposed to the sample substance.

Figure 18:
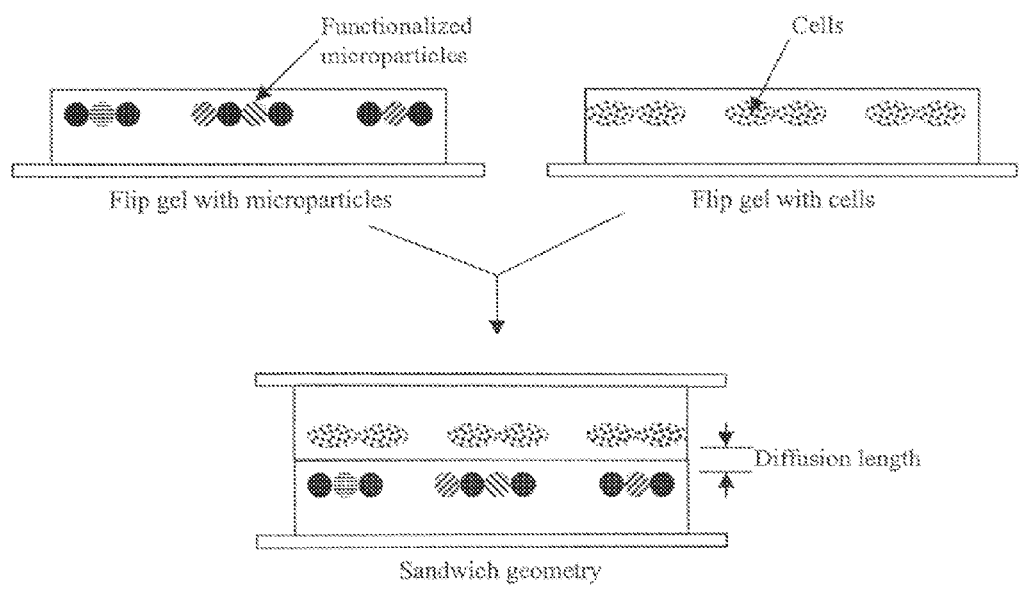
FIG. 18. is an illustration showing a gel-embedded cellular array and its use.
Figure 18:
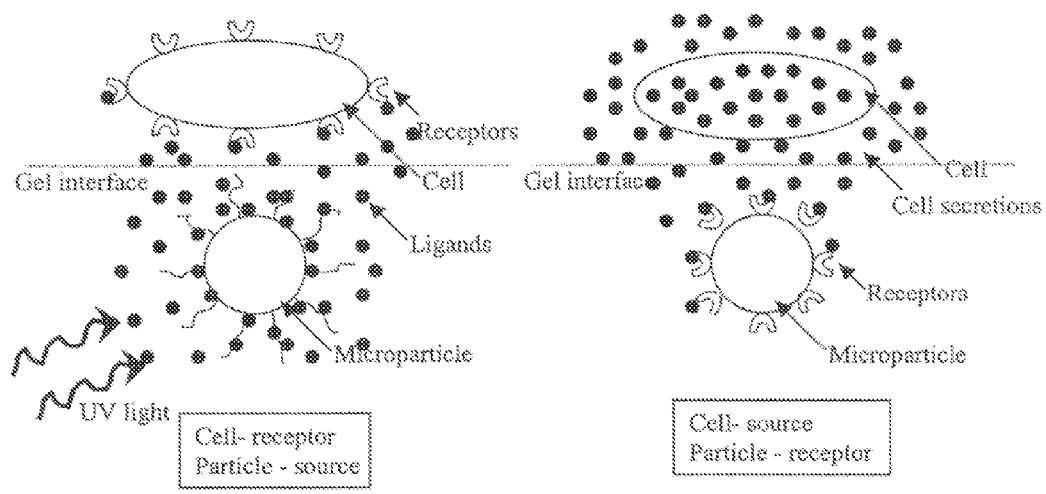

An alternative format of a functional assay, shown in FIG. 18, involves the combination of a gel-microparticle heterostructure with a gel-embedded cellular array prepared by the methods of the present invention. Embedding of cells within a thin gel film facilitates the engineering of small, functionally organized heterostuctures by avoiding the manipulation of individual cells while providing local chemistries maintaining cells in their requisite environment. The lateral spacing of cells as well as microparticles within their respective arrays is readily tuned in such a structure using LEAPS as disclosed herein.

Two separate gel films, one containing a functionalized microparticle array and the other a cellular array, are placed in direct contact in a sandwich geometry. In this configuration, particles and cells form pairs of sources and detectors of molecules to be analyzed. For example, cells can secrete molecules such as cytokines, and proximal beads within the bead array can be designed to monitor the profile, for example in a displacement assay. Alternatively, small molecules can be photochemically cleaved from an array of color-encoded beads and can be detected by monitoring the functional response of cells within the apposed gel-embedded array. The lateral patterning of the arrays as well as the short diffusion length in the vertical direction helps to prevent lateral mixing of the ligand molecules and hence enables execution and monitoring of complex local binding chemistries .

Example 17

Characterization and Control of Diffusive Transport in Gels

Figure 19:
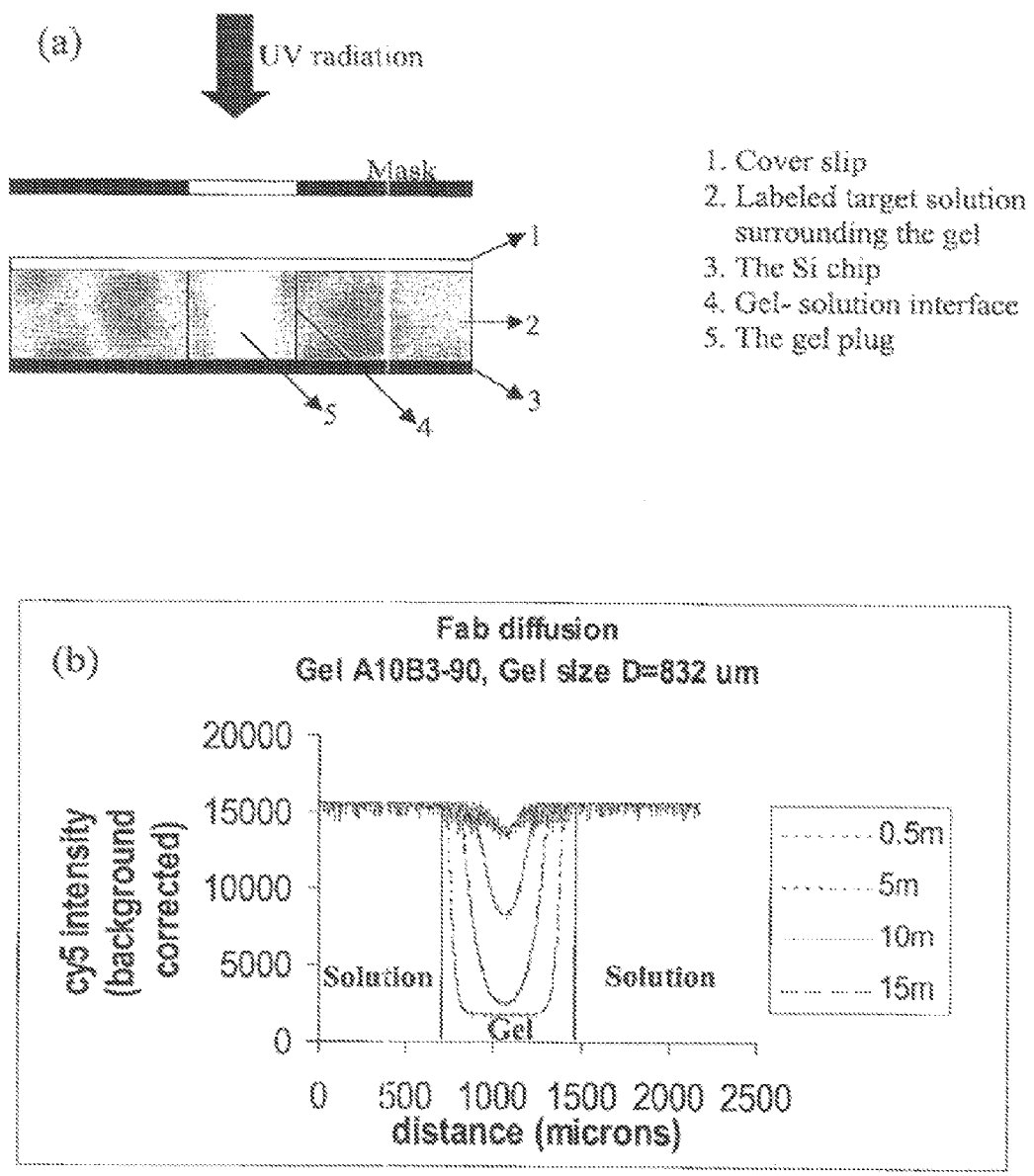
FIG. 19 shows the effect of gel chemistry and formation conditions on diffusion.

The diffusion of fluorescently tagged molecules into the gels of the present invention were studied using a sandwich cell device as illustrated in FIG. 19(a). To provide actual chemical anchoring of the gel to both the Si-chip surface and the glass coverslip both of them were pretreated using vinylmethoxysilaoxane oligomer for polyacrylamide gels, and 3-(glycidyloxypropyl)-trimethoxysilane for agarose gel, respectively.

For the coating reaction a 95% ethanol and 5% water solution was adjusted to pH 5 with acetic acid. The silane coupling agent was then added to yield 2 wt % solution. Substrates (chips and cover glasses) were dipped into the solution with gentle agitation for 5 minutes. Following, the substrates were removed from the solution and rinsed briefly in ethanol. The treated substrates were cured at room temperature 24 hours.

For the formation of the acrylamide gels the monomer mixture of 10% (w/v) acrylamide, 3% (w/v) N,N'-methylene-bis-arylamide (Polysciences, Ltd, USA), 0.1% photo initiator1-[4-2-Hydroxyethoxy)-phenyl]2-hydroxy-2-methyl-1-propane-1-one (IRGACURE® 2959, Ciba Specialty Chemicals (USA)) as well as $H_2O$ was injected into the sandwich cell. The masked cell was then exposed to an UV light source (150 W Hg) through a photo-mask for durations from 45 s up to 180 s. Following the exposure, the unpolymerized solution was removed from the cell.

For agarose gel formation, 1 µl an agarose solution (0.5% w/v) (heated to ~90C) was carefully pipetted on the surface of a pretreated Si chip, and gently covered with a pretreated cover glass slide. Under these conditions the drop of the agarose sol deforms approximately into a cylindrical plug sandwiched between the two surfaces, which turns into a gel under the room temperature conditions within 1-2 minutes. Once formed, the gel was left undisturbed at room temperature for additional 2-3 hours to promote the covalent cross-linking between the hydroxyl groups in the agarose chains and the epoxy group present on the pretreated surfaces.

Although a few exemplary embodiments of this invention have been described in detail above, those skilled in the art will appreciate that many modifications of the preferred embodiments are possible using the novel teachings and advantages of this invention. Accordingly all such inventions are intended to be included within the scope of this invention, as defined in the following claims.

What is claimed is:

1. A polymer-bead composite comprising: a single layer planar, crystalline assembly of encoded beads embedded in a hydrophilic polymeric matrix, wherein the composite is not attached to a solid support, and wherein differently-encoded beads have different biomolecules attached to their surfaces and wherein the encoding permits distinguishing of beads having different biomolecules attached thereto from each other.

2. The polymer-bead composite of claim 1 wherein the beads are encoded with a unique chemical or physical characteristic.

3. The polymer-bead composite of claim 2 wherein the encoding is with a fluorescent dye.

4. The polymer-bead composite of claim 1 wherein the biomolecules are peptides, proteins, nucleic acids, oligonucleotide, ligands or receptors.

5. The polymer-bead composite of claim 1 wherein the hydrophilic polymeric matrix is alkylacrylamide or hydroxyacrylalkylate hydrogel.

6. The polymer-bead composite of claim 1 wherein the beads are magnetic beads.

7. The polymer-bead composite of claim 1, wherein the beads are assembled in a hexagonally crystalline configuration.

8. The polymer-bead composite of claim 1, wherein the beads are assembled in a bubble raft arrangement.

* * * * *